(12) United States Patent
Marcoz et al.

(10) Patent No.: US 12,048,805 B2
(45) Date of Patent: Jul. 30, 2024

(54) METERED DOSE INHALER ADD-ON DEVICE, OBSERVANCE IMPROVEMENT SYSTEM AND METHOD FOR IMPROVING OBSERVANCE OF USE IN METERED DOSE INHALERS

(71) Applicant: Biocorp Production, S.A.S., Issoire (FR)

(72) Inventors: Alain Marcoz, Issoire (FR); Emmanuel Jez, Issoire (FR); Sylvain Diogo, Issoire (FR); Patrice Gourbet, Issoire (FR); Alexandre Pereira, Issoire (FR); Mathieu Pollard, Issoire (FR); Kevin Gillet, Issoire (FR)

(*) Notice: Subject to any disclaimer, the term of this patent is extended or adjusted under 35 U.S.C. 154(b) by 0 days.

(21) Appl. No.: 18/156,429

(22) Filed: Jan. 19, 2023

(65) Prior Publication Data
US 2023/0149644 A1    May 18, 2023

Related U.S. Application Data

(63) Continuation of application No. 16/092,782, filed as application No. PCT/IB2016/052070 on Apr. 12, 2016, now Pat. No. 11,590,300.

(51) Int. Cl.
*A61M 15/00* (2006.01)

(52) U.S. Cl.
CPC ...... *A61M 15/009* (2013.01); *A61M 15/0021* (2014.02); *A61M 15/0083* (2014.02); *A61M 2205/3327* (2013.01); *A61M 2205/3331* (2013.01); *A61M 2205/3584* (2013.01); *A61M 2205/52* (2013.01); *A61M 2205/581* (2013.01);
(Continued)

(58) Field of Classification Search
CPC .. A61M 15/009; A61M 15/0021–0026; A61M 15/008; A61M 15/0083; A61M 2205/3327; A61M 2205/3331; A61M 2205/3584; A61M 2205/52; A61M 2205/581; A61M 2205/583; A61M 2205/8212; A61M 2016/0027; A61M 2205/332
See application file for complete search history.

(56) References Cited

U.S. PATENT DOCUMENTS 5,809,997 A * 9/1998 Wolf ................. A61M 15/0005
128/200.23
9,468,729 B2 * 10/2016 Sutherland ........ A61M 15/0065
(Continued)

*Primary Examiner* — Elliot S Ruddie
(74) *Attorney, Agent, or Firm* — Patshegen IP; Moshe Pinchas

(57) ABSTRACT

An add-on device for a metered dose inhaler, an observance improvement system, and a method for improving observance of use in metered dose inhalers, the add-on device comprising an observance system housing component comprising an observance system with at least one pressure sensor; a mouthpiece component configured to fit, surround and removably engage with an exterior surface of a mouthpiece outlet provided on the metered dose inhaler; wherein the observance system housing is configured to fit and removably engage with the mouthpiece component; and the mouthpiece component is specifically adapted to conform to the exterior surface of the mouthpiece outlet of the metered dose inhaler without obstructing delivery of a dose of drug through the outlet.

17 Claims, 10 Drawing Sheets

(52) U.S. Cl.
CPC .............. *A61M 2205/583* (2013.01); *A61M 2205/8212* (2013.01)

(56) References Cited

U.S. PATENT DOCUMENTS

| | | | | |
|---|---|---|---|---|
| 2011/0253139 A1* | 10/2011 | Guthrie | ............ | A61M 15/0005 |
| | | | | 128/203.14 |
| 2013/0008436 A1* | 1/2013 | Von Hollen | ........ | A61M 15/009 |
| | | | | 128/200.14 |
| 2013/0269685 A1* | 10/2013 | Wachtel | ............ | A61M 15/0065 |
| | | | | 128/200.14 |

\* cited by examiner

METERED DOSE INHALER ADD-ON DEVICE, OBSERVANCE IMPROVEMENT SYSTEM AND METHOD FOR IMPROVING OBSERVANCE OF USE IN METERED DOSE INHALERS

The present invention relates to hand-held metered dose inhalers, also known as MDIs, and more particularly to improving the observance of treatment regimes involved in the use of hand-held metered dose inhalers to dispense a metered quantity of drug. Such metered dose inhalers generally comprise a hollow body, into which a cartridge is inserted. The cartridge contains the drug to be dispensed or delivered, and the drug is generally formulated in such a way that when the cartridge dispensing mechanism is activated, the drug is released as an aerosol of drug particles or drug solution particles suspended in a gaseous vehicle, or the solution of drug is finely dispersed when released from a high pressure environment, such as the cartridge, to a lower pressure environment, such as the ambient environment of the user of the device.

One of the biggest problems with such devices is that, although they distribute metered, i.e. known predetermined quantities of active drug substance, it is very difficult to know whether the drug has been dispensed or delivered in accordance with the recommendations of the manufacturer or health care specialists that prescribe the treatment. This can lead to circumstances where the drug is not inhaled correctly by the user, e.g. through lack of correct coordination between activating release of the drug and inhaling, or simply wasted, for example in the case of accidental delivery of the drug, or even overdosed, for example, because the user thinks that previous attempts to inhale the drug have failed or were unsatisfactory. As such devices are often used for long periods of time, e.g. to correct or treat long term respiratory conditions such as asthma, the incorrect administration and usage of such hand-held metered dose inhalers can lead to other, more serious problems.

Several attempts to exert greater control over the delivery of the drug to be inhaled and provide some measure of reassurance, feedback or comfort to the user have been proposed over the years. Most of these attempts have focused at either integrating sensors and circuitry directly into the hollow body that receives the cartridge containing the drug to be dispensed, termed here for ease of understanding as the "integrated approach", or else relate to devices that are added in some way to the hollow body or cartridge. The latter solutions are termed "add-on" devices, because they can generally be added or removed from the hollow body, or cartridge, as and when needed, or say, for example, for cleaning or exchange of the device circuitry.

An example of the integrated approach is disclosed in European patent EP0617762. A hollow body is provided in which a drug dispensing cartridge is inserted, wherein the hollow body is equipped with an observance system, including visual and audible signals, and a display, to display messages to the user with regard to correct administration of the drug dispensed by the cartridge. The body is also provided with a channel or conduit, that allows for passage of air from the outside or ambient air, to pass through the hollow body and into a drug distribution mouthpiece outlet. Electronic sensor means are located within the channel in order to measure changes in air pressure flowing through the channel, and motion sensor means are provided for detecting if the canister is shaken prior to each actuation. The various signals obtained from the various sensor means are processed and relayed to the display to show an appropriate message to the user. The problems with such a system and device are that they require a special hollow body to be manufactured to contain all of the microcircuitry, on the one hand, the extra air passage for air flow measurement, on the other hand, and that as a result, the hollow body becomes so voluminous that it can be hard to handle properly, especially, say, in the hands of children, who are most at risk of not observing their treatment regime correctly.

An example of the "add-on" device approach is disclosed in European patent EP0387222. This document describes a metered dose inhaler system that comprising a pressure filled canister and hollow body for containing said canister. The pressure canister is provided with a nozzle and is placed in a bracket with a nozzle. The bracket is shaped with a separable unit, which comprises a detector in connection with the air channel for the inhalation flow and an electronic unit. When the patient inhales from the mouthpiece, air flows are opened past the gap around the pressure canister and out through the mouthpiece. The patient has to, during the introductory phase of the inhalation, press the canister down, so that a dose is released through the nozzle. The air flow around the canister and the bracket give rise to a noise, which can be detected by a noise detector. When a dosage is released through the nozzle a sound arises, which can be distinguished from the noise and can be detected by the detector. Since these sounds are different from each other, a microphone can be used as detector. At inhalation through the inhaler according to FIG. 7, a pressure drop is created between the ambient pressure and the pressure at the mouthpiece opening, i.e. a sub-pressure arises inside the bracket when the patient inhales, which sub-pressure can be detected by a pressure transmitter. At the release of a dose, a strong pressure change with short duration arises, which is also detectable by a pressure transmitter. In the embodiment according to FIG. 7, a pressure transmitter can also be used for detection of both the inhalation and the release of a dose, i.e. the information necessary for controlling that the patient uses the dose aerosol in the prescribed way.

Another example of an add-on device can be found in European patent EP146172. This document discloses an add-on for a dry powder inhaler (DPI) as opposed to a metered dose inhaler (MDI). The dry powder inhaler in this document includes a sensor to detect that a patient has carried out an inhalation, an on/off switch, a power supply, an element for controlling means for generating an audible signal, or a light signal, via the supply of electricity to said means, when the sensor senses an inhalation by the user, and when the device is switched on. The means for generating an audible or light signal is configured to determine the strength and frequency of inhalations, and for generating light and sound signals based on the value of the determined strength and frequency of the inhalations, in order to inform the patient that they have reached the proper breathing pattern.

Another example of an add-on device can be found in U.S. Pat. No. 5,794,612, which discloses an inhalation chamber that is added to the mouthpiece outlet and which forms a supplementary chamber for inhalation other than the chamber formed by the mouthpiece outlet of the metered dose inhaler. This supplementary chamber is equipped with an ultrasound sensor and a differential pressure sensor, and microcircuitry for storing and displaying information to the user.

U.S. Pat. No. 5,809,997 discloses yet another add-on device that is screwed onto the back of the hollow body of the metered dose inhaler, and which also requires modification of the hollow body, to allow a strain gauge arm to be inserted into the back thereof for engaging a portion of the cartridge next to the valve stem provided on said cartridge. The role of the sensing arm is to communicate data to the microprocessing circuitry included in the add-on device, to allow determination of whether the cartridge is properly compressed for release of drug. The problem with this device is that it requires specific modification of the hollow body, i.e. the integrity of the hollow body, as provided by the metered dose inhaler manufacturer is necessarily destroyed.

U.S. Pat. No. 8,807,131 discloses yet another add-on device for metered dose inhalers, wherein one of the variants of the device comprises an exterior housing for microcircuitry and a communications module, and a sensor connected to the housing which is placed inside the hollow body housing the drug cartridge, whereby the sensor is located within the chamber of the mouthpiece outlet. The sensor in this mode of execution is a temperature sensor to detect changes of temperature when the user inserts, or withdraws the mouthpiece outlet, into or from the user's mouth, or when drug is released from the cartridge, as the release of drug from the pressurised cartridge also causes a change in temperature that is alleged to be detectable by the temperature sensor.

US patent US2007023034 discloses a removable add-on device for improving observance of metered dose inhaler administration, wherein the device is fitted to the heel of the hollow body that receives the drug cartridge. The compliance monitor is located underneath the heel of the hollow body. The rubber housing of the compliance monitor includes a battery, a switch, an electronics module, a temperature sensor, and a set of contacts. The battery, electronics module, switch and contacts are mounted on a printed circuit board, and a temperature sensor is mounted at the end of a protruding portion of the rubber housing which extends along an underside of the metered dose inhaler mouthpiece. The switch is covered by a flexible of rubber housing, to enable the switch to be depressed. The electrical contacts are covered by an openable portion of the rubber housing which can be removed or opened when the compliance monitor is placed on a docking station. Once again, the solution proposed in this document requires the hollow body to be modified, in this case, cut away, in order to allow the compliance monitor to be seated flush with the metered dose inhaler.

According to PCT patent application WO2011083377A1, an add-on device for metered dose inhalers is disclosed that fits around an mouthpiece outlet of the MDI, and includes microcircuitry and sensors and display means for providing feedback to a user. The hollow body of the MDI sits within the add-on device, held by a flexible inner portion mounted and supported within rigid housing. The flexible inner portion includes walls which define an aperture structured to receive the mouthpiece outlet of the hollow body of the MDI. The device includes a mouthpiece on a front end of the housing such that a central channel for medication flow is created within the housing. The mouthpiece of the housing creates a further chamber through which the drug must flow after release from the cartridge and into the mouthpiece outlet of the MDI.

All of the solutions presented above have their disadvantages. In the case of the completely integrated approach, the hollow body has to be modified to allow inclusion of all the necessary circuitry and sensors, and screens or control buttons, thereby increasing its bulk and making it potentially difficult for users with small hands to manipulate the device correctly. Where such devices integrate screens and buttons for user interaction with the device, the relative bulk must nonetheless still be kept to a minimum, thereby presenting problems for people with large hands, or just generally, people with hand coordination and movement precision problems. In the case of the add-on device approach, none of the devices currently known to the applicant allow for simple manipulation of the device when attached to the MDI, whilst at the same time allowing for accurate observance and compliance data gathering and reporting. One of the objects of the present invention is therefore a metered dose inhaler observance add-on device which overcomes the difficulties associated with the prior art devices. As will be described further below, another object of the present invention is a method for improving observance of delivery of a drug delivered via a metered dose inhaler, using an add-on device according to the present invention. A still yet further object of the invention is a metered dose inhaler observance system. Further objects of the invention will become apparent as and when they are presented or discussed in the further description and claims.

As indicated above, one object of the present invention, is a metered dose inhaler observance add-on device adapted to be removably mountable onto an exterior surface of a metered dose inhaler, said add-on device comprising:
an observance system housing component comprising an observance system with at least one pressure sensor;
a mouthpiece component configured to fit, surround and removably engage with an exterior surface of a mouthpiece outlet provided on the metered dose inhaler; wherein
said observance system housing is configured to fit and removably engage with said mouthpiece component or vice versa; and
said mouthpiece component is specifically adapted to conform to the exterior surface of the mouthpiece outlet of the metered dose inhaler without obstructing delivery of a dose of drug through said outlet.

From the above, it is to be understood that the MDI observance add-on device is therefore comprised of two main components:
a first component, which is a housing component for housing an observance system; and
a second component, which is a mouthpiece component configured to fit, surround and removably engage with an exterior surface of a mouthpiece outlet provided on the metered dose inhaler.

In the present application, the word "inner" is interchangeable with the word "interior", and the word "outer" is interchangeable with the word "exterior".

In accordance with an object of the present invention, the observance system housing component is configured to fit and removably engage with said mouthpiece component, or vice-versa, i.e. the mouthpiece component is configured to removably engage with said observance system housing component. The end result is that each one of either the observance system housing component and the mouthpiece component can engage with, or be removed from, the other component. Various means for achieving this removably or releasably engaging connection and detachment of the two components are envisaged, such as for example, at least one or more of a tongue and groove means, a clip fit means, a mortice and tenon means, a slot and projection means, and other similar releasable systems known generally in the art. One of the advantages of such a releasably attachable and detachable, or engaging and disengaging system provided either on the observance system housing or the mouthpiece component or both is that this enables the user to disassemble, as and when required, the various components, of the add-on device, say for example, to clean the mouthpiece component. Further advantages in such a releasably engaging and disengaging system between the housing component and the mouthpiece component are that it enable the manufacturer of the device to manufacture a single observance system contained with the housing and multiple mouthpiece components configured to fit, surround and removably engage with an exterior surface of a mouthpiece outlet provided on the metered dose inhaler. This in turn means that the manufacturer can provide a single observance system housed within the housing for multiple types of brand of metered dose inhaler because each MDI manufacturer tends to have slightly different mouthpiece outlet shapes according to the model and drug to be dispensed of their own range of MDIs.

It will also be understood from what precedes that the observance system housing component does not need to couple with, or connect to, any part of the hollow body of the metered dose inhaler, nor is it necessary to modify said hollow body to allow for the add-on device to be mounted on the MDI. Only the mouthpiece component is configured to fit, surround and removably engage with an exterior surface of a mouthpiece outlet provided on the metered dose inhaler, and as mentioned above this can preferably be adapted to fit, surround and removable engage with each and any of the models of MDI mouthpiece outlets currently available or to be developed in the future.

In one embodiment, the mouthpiece component extends only as far as a proximal or buccal extremity of the mouthpiece of the MDI. Preferably, said mouthpiece component has a proximal or buccal extremity that aligns with, or is slightly withdrawn from, the proximal extremity of the mouthpiece of the MDI. In this way, no supplemental chamber is created through which the drug would have to pass, in addition to the chamber already provided by the MDI, thereby reducing the risk of more aerosol-borne drug than usual being deposited on the walls of the supplemental chamber or not reaching its target due to the extra flight path length. The lack of extra or supplemental chamber, which supplemental chamber is known from the prior art solutions, also means that the mouthpiece component does not obstruct the mouthpiece outlet, nor interfere with the flow of drug to the user. As most metered dose inhalers have particular flow characteristics required for correct delivery of the drug formulation to the user, this is a noticeable advantage of the add-on device of the present invention over known systems.

In the present application, a proximal or buccal extremity of the mouthpiece of the MDI is defined as being the end or tip of the mouthpiece that is closest to the mouth of a user.

According to another embodiment of the present invention, said mouthpiece component and said observance system housing component form an air flow passage when assembled together, and the at least one pressure sensor of the housing component is located at a position along said air passage. The air flow passage is configured in such a way as to allow air to flow from outside of the observance system housing component, through said housing component and then through at least part of the mouthpiece component. Preferably, the air flow passage formed by the observance system housing component and the mouthpiece component, is defined such that when the add-on device is mounted on the mouthpiece outlet of the MDI, said airflow passage extends at least partly along the exterior surface of the mouthpiece outlet of the MDI in the direction of the proximal or buccal extremity of said MDI.

In one embodiment, said airflow passage extends along the exterior mouthpiece outlet of the MDI all the way to the proximal or buccal extremity of said mouthpiece outlet of the MDI.

In another embodiment, a proximal zone of the air flow passage is formed from the space created between an inner groove surface of the mouthpiece component and a corresponding outer or exterior surface of the mouthpiece of the metered dose inhaler. Alternatively, the air flow passage in the mouthpiece is defined by a channel or conduit provided directly within the material constituting the mouthpiece component itself, said conduit extending all the way to a proximal or buccal extremity of said mouthpiece component. In another alternative embodiment, the air flow passage is defined by a plurality of openings in the inner surface, extending all, or only part, of the way to the proximal or buccal extremity of said mouthpiece component. The objective of having an air flow passage extend all, or at least part of the way, along the inner surface of the mouthpiece component is to enable air to be sucked along said passage as the user inhales, or alternatively, blown back along said passage, as the user exhales, or stops inhaling, thereby causing a slight blowback in air pressure along said air passage. Indeed, the treatment provided by most inhalers works on the principle that a user breathes in, or inhales the drug delivered by the cartridge through the MDI mouthpiece outlet, and then the user stops inhaling and holds their breath for a while, usually a few seconds or more. The step of stopping inhalation causes a minute air pressure change within the air flow passage, that the first pressure sensor will detect. At the end of the allotted time, usually counted manually in the user's head, via a watch or other timing device, or on their fingers for example, with children, the user exhales. The exhalation step usually takes place with the MDI removed from the user's mouth, however, it can often occur that the user finds it impossible or too difficult to hold their breath for the allotted or recommended and time, and is not quick enough to remove the MDI from their mouths before exhaling. This can result in air being blown back along the air flow passage. Again, the first pressure sensor will detect this change.

In yet another embodiment, a distal zone of the air flow passage is formed by an opening in an outside wall of the observance system housing leading to the local atmospheric environment outside said housing, and located in direct alignment with said first pressure sensor. In this embodiment, the air flow passage in the distal zone, i.e. the zone in which air is generally withdrawn into the device on user inhalation, allows air to flow in via the opening of the outside wall of the observance system housing, and from there over the first pressure sensor, where a change of air pressure will be detected due to said air flow, and then through the remainder of the air flow passage leading to the buccal or proximal region, or extremity, of the mouthpiece component.

In an alternative embodiment, a distal zone of the air flow passage is formed by an opening in the observance system housing located at a distal extremity of said housing. Such an opening could be represented, for example, by the opening in the outside wall of the observance system housing at the location of a communications port, such as a USB port, micro-USB or mini-USB port, or alternatively, be represented by a one or more openings, such as a plurality of openings made elsewhere in the outside wall of said observance system housing.

According to yet another embodiment, an intermediate zone, located between a distal zone and a proximal zone of said air flow passage is provided in part in the observance system housing and located at a proximal extremity of an outside wall of said housing, and in part by a space created at a distal extremity of said mouthpiece component, the two parts being in direct air flow contact one with the other to form said intermediate zone. The intermediate zone therefore comprises both a proximal opening of the observance system housing and a distal extremity space of the mouthpiece component.

Preferably, the intermediate zone is formed by an orifice in the observance system housing which is in direct air flow communication with a distal extremity of the inner groove surface of the mouthpiece component.

In another preferred embodiment, the distal extremity of the inner groove surface of the mouthpiece component is defined by a cut out section of a projecting connector tongue of the mouthpiece component.

The total length and shape of the air flow passage is defined in such a way as to provide an appropriate sensitivity to pressure change detectable by the first pressure sensor when air flows through the passage either from the distal zone or distal extremity towards the proximal zone or proximal extremity, or vice-versa, and over or through said first air pressure sensor.

In still yet another embodiment, the mouthpiece component configured to fit, surround and removably engage with an exterior surface of a mouthpiece outlet provided on the metered dose inhaler, has a substantially annular shape. The applicant has determined that a generally annular shape has been found to be the most advantageous shape for the mouthpiece component, as it allows for a snug elastic, or friction-based, fit to be implemented, so that the mouthpiece component can be slid onto, around and engage with an outer or exterior surface of the mouthpiece outlet of the MDI. The substantially annular shape of the mouthpiece component also enables said component to be easily designed to adapt to the contours of any of the available mouthpiece outlets of the MDIs currently available or to be developed in the future.

To this end, and in another embodiment, the mouthpiece component has a substantially annular shape which is defined by an inner and an outer peripheral walls joined together to form the annular shape, the inner peripheral wall of the mouthpiece component engaging with an exterior surface of the mouthpiece outlet.

In still yet another embodiment, the inner peripheral wall of the annularly shaped mouthpiece component is provided with grip means for engaging elastically with the exterior surface of the mouthpiece outlet. Such grip means can be provided in several different ways, for example, using at least one or more chosen from the group consisting of cushions, pads, strips, ribs, grooves, stipples, or any other equivalent grip means to ensure a snug elastic fit of the annularly shaped mouthpiece component onto the mouthpiece outlet of the MDI. The applicant has found that the most appropriate means for ensuring such a snug, elastic fit that enables the mouthpiece component to stay in place, yet at the same time be relatively easy to remove for the user, is elastomer based pads, positioned at selected strategic areas on the inner peripheral wall of the annularly shaped mouthpiece component. The grip means not only enable the mouthpiece component to remain correctly seated on the outer peripheral surface of the mouthpiece outlet of the MDI, but can also, dependent on their relative thickness and the depth by which they project out over the inner peripheral wall of the mouthpiece component, provide for additional passage of air between the intermediate zone and the proximal zone when the device is mounted.

According to one embodiment of the invention, the at least one, or first, pressure sensor is configured to detect at least one or more air pressure change events. The pressure sensor can be of any suitable type, for example barometric pressure sensors, of the kind often used in mobile phone technology to determine altitude, piezo-resistive pressure sensors, absolute digital pressure sensors, MEMS pressure sensors. Suitable examples of pressure sensors available in commerce are sold under the references BOSCH BMP 280, NXP MPL 115A, Amphenol NPA 201, OMRON 25MP-01-01, and ST LPS 25 HB. The preferred pressure sensor is a piezo-resistive pressure sensor, for example the ST LPS25HB sold by ST Microelectronics, France, which has been found to be particularly suitable in the add-on device of the present invention.

In another embodiment, the at least one pressure sensor is configured to measure at least one or more air pressure change events in air flowing through the airflow passage formed by the mouthpiece component and said observance system housing component when assembled together. Although the first pressure sensor is located in the path of the air flow passage, and could just be used to measure, or detect, air pressure changes at its particular location, it is preferred that this pressure sensor be configured to detect air pressure change events which occur at any point across the whole, or substantially the whole, of the air flow passage length. To this extent, the sensitivity of the air pressure sensor will be set accordingly.

In yet another embodiment, the observance system housing component further comprises a second pressure sensor. This second pressure sensor is preferably configured to register at least one or more user activated compression events of the observance system housing. In this regard, it is to be understood that a user activated compression event of the observance system housing refers to a mechanical compression applied directly or indirectly by the user to the observance system housing. Such a mechanical compression will generally occur when the user holds the MDI between finger and thumb, usually with the finger on the top of the cartridge and the thumb underneath the body of the cartridge, except that in this configuration the observance system housing will be at least partly located underneath the hollow body of the MDI, such that the thumb, or say, the palm of the hand, will press against the observance system housing and compress the latter to such an extent that this mechanical compression will be detected by the sensor.

In still yet another embodiment, the body of the observance system housing is preferably made from a semiflexible material, for example, a plastics material, suitably selected from the group consisting of ABS (acrylonitrile butadiene styrene polymer), PC (polycarbonate polymer), POM (polyoxymethylene monomer), and ABS-PC (acrylonitrile butadiene styrene polycarbonate co-polymer) whereby ABS-PC is most preferred and has been found to provide the right degree of flexibility and resistance to the forces generally applicable in such a situation. Alternatively, the observance system housing can be made of a material that can withstand a mechanical compression caused by the user applying the palm of its hand or first to the top of the cartridge and pressing down against a harder or softer surface onto which the observance system housing would bear. The body of the observance system housing is therefore made of a material that can deform elastically under the impetus of the applied mechanical compression, and this deformation will be sufficient to cause the second pressure sensor to detect that a mechanical compression of a given magnitude has occurred.

In another embodiment, the second pressure sensor can be in a connectable relationship to a pushbutton provided within the observance system housing, wherein the connectable pushbutton applies direct mechanical pressure to the second pressure sensor when the body of the observance system housing is deformed. In such a configuration, the connectable pushbutton can be affixed to an inside wall of the body of the observance system housing, and the elastic deformation imparted to the housing will cause the pushbutton to move into a connected relationship with a surface of the second pressure sensor, thereby applying either direct mechanical compression to the sensor, which will be translated into a suitable signal or data point, or alternatively, creating an electrical circuit and corresponding signal between the pushbutton and the sensor, the strength of which will be indicative of the pressure applied.

In still yet another embodiment, the observance system housing further comprises a motion sensor.

In a preferred embodiment, the motion sensor is configured to register, when the add-on device is mounted on the metered dose inhaler, at least one or more voluntary user-induced vibration events of the metered dose inhaler above a predetermined level of movement.

In another embodiment, the motion sensor is configured to detect movement imparted by the user, above a certain level, and thereby allow the observance system to be switched on or off, or sleep. The motion sensor is preferably configured to ignore any levels of movement below a set level, and register any levels of movement that exceed that threshold or set level.

One preferred way in which detection of the required level of movement can be achieved is through the use of an accelerometer as the motion sensor. Appropriate motion sensors can suitably be selected from those motion sensors available in commerce under the references BOSCH BMA 455, Analog device ADXL 363, NXP FXL 58471 8471 and ST LIS2DH, where the motion sensor sold by ST Microelectronics under the reference ST LIS2DH is particularly suitable.

According to still yet another embodiment of the invention, the motion sensor is configured to register at least one or more predetermined acceleration movements of between about 1G to about 3G and preferably 2G to 2.5G. Preferably, said motion sensor is configured to register at least two to five successive acceleration movements, each of the two to five successive acceleration movements being within the range identified above.

In yet a further embodiment, the observance system housing further comprises a micro-controller, and at least one or more elements selected from a data storage means, a visual signal producing means, an audible signal producing means, a power supply, a wireless communications module, and a communications port, each of said at least one or more elements being connected to said micro-controller. The microcontroller can be selected from any suitable programmable micro-controllers, but preferably said microcontroller is chosen from the following commercially available micro-controllers: Broadcom BCM 20736S, containing an integrated bluetooth module and antenna, Broadcom BCM 20732S, containing an integrated bluetooth module and antenna, Cypress PSSoc 4xx7 containing an integrated bluetooth module, STM 322 equipped with an external bluetooth BlueNRG circuit, Nordic semiconductor NRF 51 with integrated bluetooth module, and Nordic semiconductor NRF 52 with integrated bluetooth module. A preferred micro-controller from the previous list is the Nordic semiconductor NRF 52.

The device can be configured to be able to function in different ways depending on the desired application of the device and particular model or brand of MDI with which the device is supposed to interact, or be adapted to. In particular, according to one embodiment, the device can remain in an off state, whereby most of the components of the observance system is not powered by a power supply, or the system is maintained in a state of sleep. The motion sensor is configured, for example, to only detect movements that correspond to an acceleration of between about 1G to about 3G, and then only relay that information to the micro-controller if two to five successive movements of acceleration of between about 1G to about 3G each are detected. When such a number of successive movements of acceleration falling within the above range each are detected, the micro-controller receives this information and reacts thereto by allowing the rest of the system to be woken up and powered by the power supply via the micro-controller. Alternatively, the whole device can be maintained in an unpowered, or off state, until such time as the user requires delivery of drug from the MDI and then commutes an appropriately included power switch provided in the add-on device, and connected to the observance system.

In accordance with another embodiment, the micro-controller is configured to determine whether the at least one or more vibration events registered from the first motion sensor corresponds to a voluntary user-induced vibration event of the metered dose inhaler, and thereby determine if the metered dose inhaler has been primed for a drug delivery. Indeed, the two to five successive movements of acceleration are considered to correspond precisely to a user shaking the MDI to prepare or prime the aerosol in the cartridge for delivery, as per the usual user instructions for use of the MDI, and prior to release of the drug formulation. These movements of acceleration are picked up by the motion sensors, as described above, and relayed to the microcontroller.

According to still yet another embodiment, the micro-controller is further configured to register a pressure change event at the second pressure sensor caused by a user activated compression of the observance system housing.

In yet another embodiment, the micro-controller is further configured to determine whether the pressure change event registered at the second pressure sensor corresponds to a user-activation of drug delivery. The micro-controller is thus configured to be able to determine whether or not the MDI has been activated by the user to release the drug, for example, by pressing down on the cartridge and causing the valve thereof to release drug into the mouthpiece outlet of the MDI. This detection is effected via registration of the mechanical compression pressure or force applied to the second pressure sensor as described above in the section relating to the second pressure sensor.

Bearing in mind that a user could accidentally press down the cartridge, and cause the housing component to be compressed mechanically, thereby causing a signal to be produced that would indicate that the drug had been released, the micro-controller is further configured to determine whether the vibration event registered from the first motion sensor, and the pressure change event registered at the second motion sensor, correspond to a user action of priming and pressing a drug cartridge of the metered dose inhaler to release drug through the mouthpiece of the metered dose inhaler. In other words, the micro-controller is configured to check that the MDI has been correctly primed and the drug released via application of suitable pressure on the cartridge, which corresponds to a mechanical compression force or pressure imparted to the second pressure sensor contained within the observance system housing component.

As a further embodiment, the micro-controller is configured to register a time of occurrence of a pressure change event registered at the second pressure sensor and a time of occurrence of a pressure change event registered at the first pressure sensor, and then record all data and corresponding event times received from said first and second pressure sensors in a rolling buffer for a predetermined window of elapsed time. Preferably, the buffer having a predetermined window of elapsed time is defined by the time registered upon occurrence of a pressure change event registered at the second pressure sensor minus a buffer margin that can range from between 0.5 to 1.5 seconds, and added thereto is a listening window of 5 seconds, during which window of elapsed time all pressure sensor event occurrences received from said first and second pressure sensors are recorded by the micro-controller and stored in memory.

According to yet another embodiment, the observance system housing is preferably equipped with timer means, enabling a time to be registered of the occurrence of any given sensor event. The timer means can be included in the micro-controller, for example, the latter can contain a real time clock, which is then used as a reference for registering relative times of events occurring at and registered by the sensors.

The timer means, micro-controller and pressure sensors therefore cooperate to capture data, and from the data captured, via the remote system or device executing the software application, enable calculation, from the event time of the pressure change at the second pressure sensor, i.e. the mechanical compression event, of how much time has elapsed between pressing the cartridge to release the drug, and the change in pressure in the air flow passage caused by inhalation by the user of the drug through the mouthpiece outlet of the MDI. The time and degree of pressure change is indicative of the quality of the inhalation, and can be correlated to an ideal drug delivery release over time window. As the micro-controller is further configured to take multiple readings of pressure from the first pressure sensor, and can correlate that to elapsed time, the pressure values over time curve can be calculated and stored in data storage within the observance system of the add-on device and from there communicated to the software application executing on the remote system.

Once sufficient data has been gathered, as mentioned above, a further embodiment of the invention provides that the data stored in data storage can be communicated via data exchange to a software application running on a remote device, or remote system such as a server, or distributed network system, for example, on a smartphone. The software application is programmed to display the data received in a manner easily understandable by the user or an appropriately qualified healthcare individual.

Consequently, accord to another embodiment, data exchange occurs via the wireless communications module, or via the communications port. The wireless communications module, which can comprise for example a Bluetooth low energy circuit, can use any of the known protocols and means for data transmission, or a bespoke protocol as required and designed specifically for the add-on device and observance system. Where a wireless communications module is not required, data exchange can be effected between the add-on device and another system via the communications port, for example, via a USB, micro-USB or mini-USB port, or any other suitable communications port.

In still yet another embodiment, the micro-controller is further configured to manage the observance system's power supply, including switching the system on and off, keeping the system in a state of slumber or in the awake state, and the like.

As mentioned above, the communications port can be configured for communication and exchange of data between the observance system in the add-on device and a remote device or system, but can also be configured to enable recharging of the observance system's power supply. Alternatively, the observance system can also comprise a wireless charging circuit as desired.

According to yet another object of the invention, the invention relates to a metered dose inhaler fitted with an observance system add-on device as described according to the various embodiments and details indicated above.

Still yet another object of the present invention is a method for improving observance of delivery of a drug delivered via a metered dose inhaler, said method comprising:

fitting an observance system add-on device, as described according to the various embodiments and details indicated above, to a mouthpiece outlet of a metered dose inhaler;

configuring the add-on device to turn itself on when a vibration event of a particular magnitude is registered by a micro-controller provided on said add-on device received from a motion sensor provided on said add-on device;

configuring the add-on device to detect a pressure change event at a second pressure sensor provided on said add-on device and corresponding to pressing a drug cartridge of the metered dose inhaler to release drug through the mouthpiece of the metered dose inhaler;

configuring the add-on device to detect onset of inhalation via a pressure change event registered at a first pressure sensor provided on said add-on device;

configuring the add-on device to detect an end of inhalation via a pressure change event at said first pressure sensor;

communicating data pertaining to at least one sensor event to a software application executing on a remote device, a remote server or a distributed network system;

presenting said data to a user of the device or a healthcare professional in a manner enabling said user or healthcare professional to see whether the drug has been inhaled correctly.

The method indicated above is not only an improvement over existing known add-on devices, it is also much simpler to use, and provide feedback to the user rapidly, without over-complicating manipulation of the device, or obstructing normal function of know MDIs. In fact, the method implemented according to the present invention keeps use of the MDI to exactly the same routine to which the user has become accustomed, without losing the benefit of information feedback and observance data.

According to one embodiment of this object, the method further comprises configuring the add-on device to activate a visual signal or audible signal indicating correct level of remaining power supply, and/or that the device is in a state ready to be used.

According to another embodiment of said object, the method further comprises configuring the add-on device to activate a visual signal or audible indicating correct priming of drug to be delivered.

According to still yet another embodiment of this object, the method further comprises configuring the add-on device to activate a visual signal or audible signal or both, indicating correct inhalation of drug delivered through the mouthpiece.

In a yet another embodiment, the method further comprises configuring the add-on device to activate a visual signal or audible signal or both, indicating the location and/or position of the add-on device. The aim of this embodiment is to facilitate location of the add-on device and, when it is mounted on the MDI, said MDI, in the eventuality that the user misplaces said device or MDI. The remote device, for example, a smartphone executing corresponding software can detect the location of the device and send for example a location identify command to the add-on device to cause said device to reveal its whereabouts to the user, either visually, for example, via a flashing or coloured LED, or audibly, for example via the emission of an audible signal. Alternatively, the device can contain circuitry, such as a GPS emission circuit, that will allow the device to be tracked via GPS tracking software, which software can be run on the remote device, e.g. the smartphone to facilitate location of the add-on device.

Advantageously, the method according to the invention also provides for the add-on device to be further configured to store within the device a number of drug doses delivered by the metered dose inhaler.

Another embodiment in the method of the invention, is to further configure the add-on device to store within said device a number of drug doses remaining in the metered dose inhaler. This information can then be relayed to the user, for example, via the communications module or communications port to the smartphone application software, and from there relayed to the user.

According to yet another embodiment, the add-on device is further configured to store within the add-on device a power supply level.

Furthermore, the method and or device relates to an embodiment in which the add-on device is further configured to store within the device a wake up time of the add-on device.

In a similar manner, other embodiments can be envisaged, such as:
further configuring the add-on device to store within said device a priming time of said metered dose inhaler;
further configuring said add-on device to store within said device a drug release time from said metered dose inhaler;
further configuring said add-on device to store within the device a time of onset of inhalation of released drug;
further configuring said add-on device to store within the device a time of end of inhalation of released drug.
further configuring said add-on device to communicate any of the preceding data, signals or time events to a remote device, remote server or a distributed network system, wherein said remote device is a preferably a mobile telephone or smartphone.

In accordance with still yet another object of the present invention, there is provided a metered dose inhaler observance system comprising a micro-controller and at least one or more elements selected from a data storage means, a visual signal producing means, an audible signal producing means, a power supply, a wireless communications module, a first pressure sensor, a second pressure sensor, a motion sensor, and a communications port, each of said at least one or more elements being connected to said micro-controller.

The micro-controller is preferably configured to register at least one or more vibration events of a predetermined magnitude received from a motion sensor connected to said micro-controller.

The at least one or more vibration events of a predetermined magnitude received from a motion sensor connected to said micro-controller each has a movement of acceleration of between about 1G to about 3G.

The micro-controller is more preferably configured to register two to five successive vibration events received from a motion sensor connected to said micro-controller, whereby each vibration event has a movement of acceleration of between about 1G to about 3G.

The micro-controller is further preferably configured to register at least one or more pressure change events at a first pressure sensor connected to said micro-controller.

The micro-controller is further preferably configured to register at least one or more air pressure change events at a first pressure sensor connected to said micro-controller.

Said at least one or more pressure change event is most preferably the air pressure change produced at the first pressure sensor upon inhalation of a drug delivered by the metered dose inhaler.

Said at least one or more pressure change event is even more preferably the air pressure change produced at the first pressure sensor at the end of an inhalation of the drug delivered by the metered dose inhaler.

The micro-controller is preferably further configured to detect at least one or more pressure change event at a second pressure sensor connected to said micro-controller.

The at least one or more pressure change event at the second pressure sensor is more preferably a mechanical compression pressure change.

The at least one or more pressure change event at the second pressure sensor is even more preferably a mechanical compression pressure change produced by mechanical compression applied to said second sensor.

The at least one or more pressure change event at the second pressure sensor is most preferably a mechanical compression pressure change produced by mechanical compression applied directly or indirectly to said second sensor.

Said micro-controller is further preferably configured to communicate data pertaining to at least one or more sensor events via said wireless communications module or said communications port to a software application executing on a remote device, a remote server or a distributed network system.

The remote device is more preferably a mobile telephone or smartphone, and said micro-controller is further preferably configured to communicate said data to said software application, the latter being configured to present said data to a user of a metered dose inhaler device equipped with said observance system or a healthcare professional, in a manner enabling said user or healthcare professional to see whether a drug delivered by the metered dose inhaler has been inhaled correctly.

The above and other objects will be further illustrated and understood by referring to the accompanying drawings and detailed description of the embodiments of the invention, provided purely for exemplary purposes, and in which.

EXAMPLE

Figure 1:
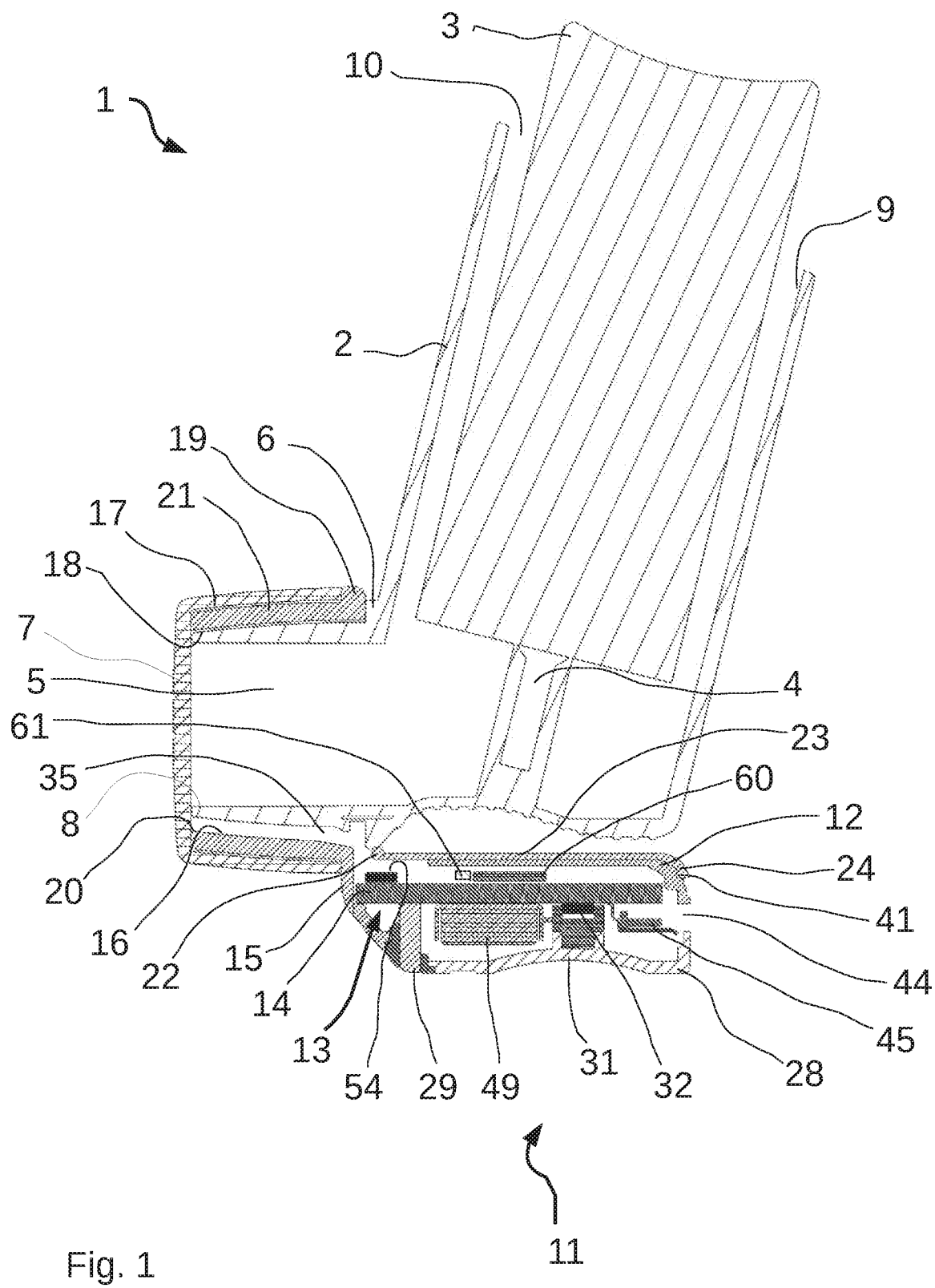
FIG. 1 is a schematic cross-sectional representation of a metered dose inhaler of known type fitted with the add-on device according to the present invention.

In FIG. 1, a metered dose inhaler, or MDI, is represented generally by the reference numeral 1. Said MDI comprises a hollow body 2, and a cartridge 3 containing a drug formulation to be dispensed. The cartridge is equipped with a valve and dispensing nozzle 4 for dispensing an aerosol drug formulation in a metered dose in the known manner. When the cartridge 3 is pressed down by a user, drug formulation is released through the nozzle 4 and into a mouthpiece outlet 5. The mouthpiece outlet 5 forms an integral part of hollow body 2, and forms an abutting shoulder 6, onto which a safety cap 7 is usually engaged in abutting relationship, thereby closing the mouthpiece outlet when the MDI is not in use. The mouthpiece outlet 5 has a proximal, or buccal, extremity 8, which is placed in the mouth of the user on inhalation of drug, as opposed to a distal extremity 9, located at an opening 10, through which the cartridge is introduced into the hollow body 2.

The metered dose inhaler observance add-on device according to the present invention is represented generally by reference numeral 11. The device 11 consists of two components in the embodiment illustrated in FIG. 1. A first component is an observance system housing component 12. The housing 12 houses the observance system represented generally by reference numeral 13. The observance system comprises various electronic or microelectronic elements or components as will be described in more detail hereafter, these elements being mounted on a printed circuit board (PCB) 14. A second component of the add-on device is a mouthpiece component 15. As is apparent from FIG. 1, the mouthpiece component is substantially annular in shape, and has an inner surface 16 and an outer surface 17, whereby the inner or interior surface 16 of the mouthpiece component 15 is engaged with and rests on the exterior, or outer peripheral surface 18 of the mouthpiece outlet 5 of hollow body 2. A distal extremity 19 of the mouthpiece component 15, is in abutment with the abutting shoulder 6 of the hollow body 2. The mouthpiece component 15 fits and engages elastically or via friction with the mouthpiece outlet 5 in such a way that said mouthpiece outlet 5 is neither obstructed, with regard to flow of drug ejected through the nozzle into the mouthpiece outlet, nor structurally modified in comparison to the available MDIs. Thus, flow and dispensing or delivery of drug from the cartridge 3 through the nozzle 4 and the mouthpiece outlet 5 is unchanged. The mouthpiece component 15 also comprises a proximal, or buccal, extremity 20, which lies flush, when the add-on device is mounted on the MDI, along a plane with the proximal extremity 8 of the mouthpiece outlet 5. In this way, there is no significant noticeable difference for the user when it inserts the MDI containing the add-on device mounted thereon into its mouth to inhale the drug. The inner 16 and outer 17 surfaces of the annularly shaped mouthpiece component together form a wall 21, the thickness of which is chosen so as to not to cause noticeable discomfort to the user when inserting the mouthpiece outlet of the MDI into its mouth. As is also apparent from FIG. 1, the mouthpiece component 15 further comprises a projection or tongue 22, which extends beyond the distal extremity 19 of the mouthpiece component, and is preferably made of the same material as the remainder of the mouthpiece component 15. The projection, or tongue 22, is generally planar, although it can also be suitably curved to match the bottom contour of the hollow body 2 of a MDI, and extends in a distal direction to form a supporting plate 23. The tongue is terminated at its own distal extremity 24 to form a retaining hook, clip, or elastic abutment, the significance of which will be explained hereafter. The supporting plate 23 and distal extremity 24 of tongue 22 are configured to allow removable engagement of the observance system housing component 12 as will be described hereafter in respect of the other figures. As is apparent from FIG. 1, the observance system housing component lies in the same plane as the tongue 22 and plate 23 of the mouthpiece component 15. This configuration, enabling removable engagement of the respective observance system housing component 12 and the mouthpiece component 15 with, and from, each other enables a single design to be maintained for the observance system housing component 12, and a variable design for the mouthpiece component 15 that can be adapted to all of the varying shapes of mouthpiece outlet 5 currently known or to be developed in future. Due to this configuration of a removably engaging mouthpiece component 15 and observance system housing component 12 as described and illustrated, the mouthpiece component 15 can also be removed for cleaning, or changed easily if the user switches to a different MDI. The removably engaging observance system housing can also be exchanged, as and when required, for example, if a defect occurs, without having to change the corresponding mouthpiece component. An increased flexibility in the use case of the add-on device is the advantageous effect of configuring the mouthpiece component and observance system housing component in this way.

Figure 2:
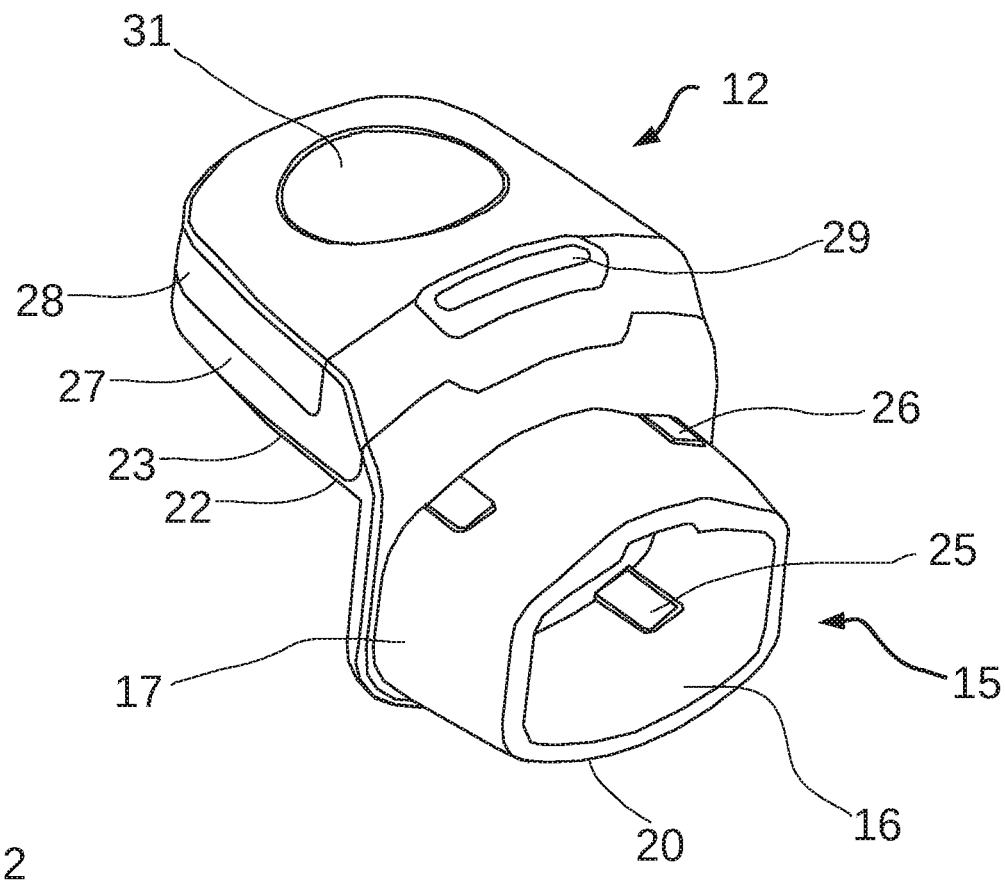
FIG. 2 is a schematic perspective view of the add-on device of the invention, from a first angle.
Figure 3:
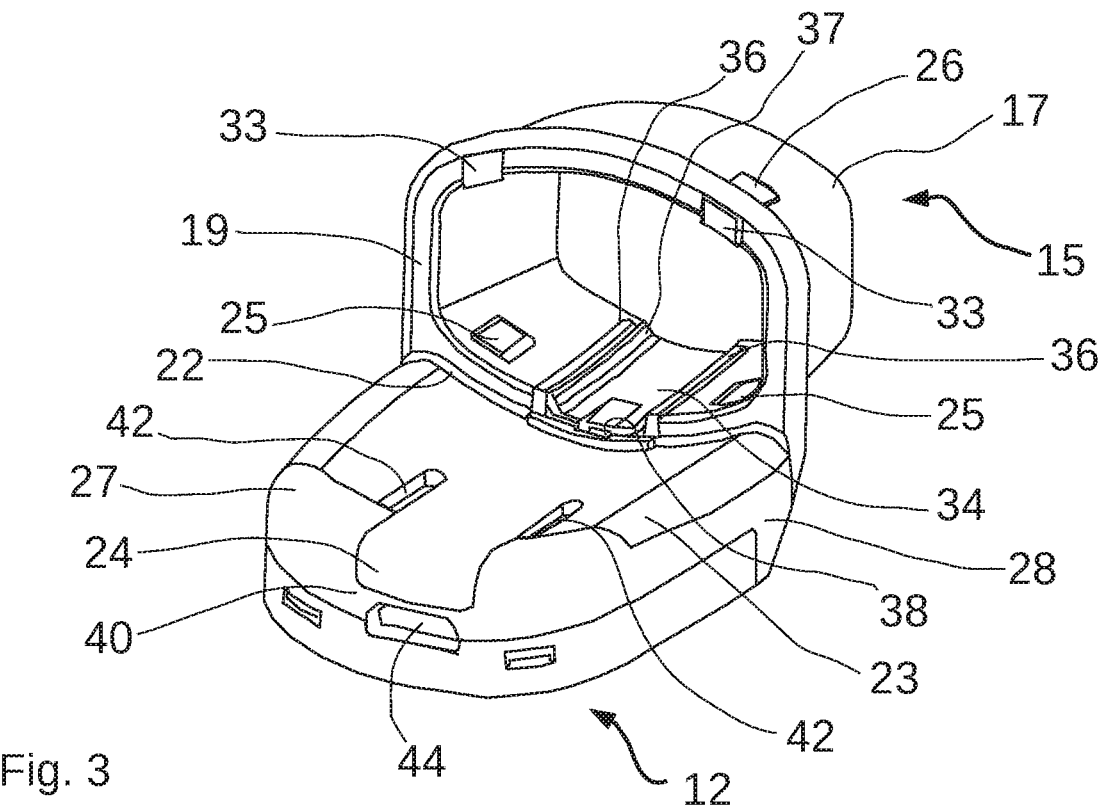
FIG. 3 is a schematic perspective view of the add-on device of the invention as represented in FIG. 2, from a second angle which is the opposite and inverted view of FIG. 2.

Turning now to FIGS. 2 and 3, an add-on device is shown from two perspective angles, FIG. 3 being a substantially reversed and flipped view of the add-on device of FIG. 2. In these representations, the respective components, i.e. observance system housing component 12, and mouthpiece component 15, are assembled together and engage with each other forming the add-on device 11. The substantially annular shape of the mouthpiece component 15 can be seen. In FIG. 2, the proximal, or buccal extremity 20 is visible as are grip means 25, for example pad or cushions, embedded in, flush with, or slightly projecting out beyond, the level of the inner surface 16, whereby the grip means 25 facilitate elastic or frictional engagement of the inner surface 16 of the annular mouthpiece component 15 with an outer, exterior, peripheral surface 18 of a MDI when the add-on device of the invention is mounted thereon. Such grips means are preferably made of elastomeric material, such as for example, those selected from the group consisting of SBS (styrene-butadiene-styrene polymers), SEBS (styrene-ethylene-butylene-styrene polymers), silicones, EPDM (ethylene-propylene-diene-monomer), rubbers, and thermoplastic elastomers (also known as TPE), such as TPE-U, a polyurethane based thermoplastic elastomer, or hydrogenated sequenced styrene block copolymers, an example of which is Thermolast® K, commercialized by Kraiburg TPE Gmbh & co, Germany. One can also see similar grip means 26 on an outer peripheral surface 17 of the annular shaped mouthpiece component 15. The grip means 26 are intended to facilitate elastic or frictional engagement of the safety cap 7 onto said outer peripheral surface 17 of the mouthpiece component 15. The frictional engagement of grip means 25 and grip means 26 is such that a user can slide the mouthpiece component 15, and respectively the safety cap 7, on and off the respective mating or engaged surfaces 17, 18, using manual manipulation only, i.e. without the assistance of tools. The grip means 25, 26 also ensure that neither the mouthpiece component, nor the safety cap 7 respectively, can simply fall off, or disengage with the respective surfaces 17, 18, for example, if the add-on device gets knocked or dropped, or receives a sudden shock or impact. FIG. 2 also illustrates part of the tongue 22 which extends to form a support plate 23 for the observance system housing component 12. The observance system housing component 12 can be seen to include a tray 27, which rests on, is supported by, and/or engages with, the plate 23, and a lid or cover 28. The observance system housing component 12 also comprises a light guide 29, for example, for a visual signal means 63 such as a LED or LED array to allow display of a suitable light signal representation various states during the functioning of the add-on device and observance system. In FIG. 2, the light guide 29 is located between the tray and the cover, but it can also be located in any suitable position, for example, on the cover 28, or elsewhere on the body 30 of the tray 27. Alternatively, the light guide could be absent, and optionally replaced or completed by an audible signal emitter, located within the observance system housing component. As is apparent from FIG. 2, the cover 28 comprises a prehensile depression 31, of a size and dimension adapted to receive a user's digit, such as a thumb. The prehensile depression 31 facilitates location of the user's digit to form a pincer movement when, in use, the add-on device being mounted on a MDI, the user presses down on the cartridge 3, causing the heel of the hollow body and the add-on device to be compressed and moved towards each other. This mechanical compression pressure generated is registered by a pressure sensor 32 located in the observance system housing component 12 in direct or indirect physical or electrical contact with the prehensile depression 31.

In FIG. 3, one can see the inner surface 16 of the mouthpiece component 15, including grip means 25 located thereon. Further grip means 33 are also provided at the distal extremity 19 of the annular shaped mouthpiece component 15, enabling frictional abutment with the abutting shoulder 7 of a MDI onto which the add-on device would be mounted. FIG. 3 also shows a channel or groove 34, extending along the inner surface 16 from the distal extremity 19 of the mouthpiece component 12 towards the proximal extremity 20 of said component. The channel or groove 34 defines at least in part, or wholly, a proximal air flow passage 35 for passage of air. When the add-on device is mounted on a MDI, the proximal air flow passage becomes airtight along said channel due to the presence of sealing means 36 provided along the walls 37 of the channel 34 and projecting out to meet and sealingly engage with an exterior peripheral surface of the mouthpiece outlet of the MDI. Such sealing means 36 can be, for example, strips of elastomeric material, such as the same material used for the grip means. At its distal extremity 19, the mouthpiece component is provided with an opening 38, which corresponds to an opening 39 (not shown in FIG. 3) provided in a proximal extremity of the observance system housing component. An air flow passage communication is thereby established from the observance system housing 12 to the mouthpiece component 15. Also shown in FIG. 3 is the tongue 22 and support plate 23, which extend in a substantially planar configuration towards a distal extremity 24. The distal extremity 24 of tongue 22 is preferably configured to form a curved lip, hook or edge, which wraps around a distal extremity 40 of tray 27, and is provided with engagement means 41 to removably engage with the distal extremity 40 of tray 27. Such removable engagement means 41 can be, for example, a snap-fit or click-fit projection provided at the distal extremity 24 of the tongue 22, and which is elastically insertable into a corresponding slot provided at the distal extremity 40 of the tray 27. The support plate 23, in the embodiment represented by FIG. 3, also shows two slots 42 provided in said plate 23. The slots 42 provide flexibility to the support plate and the tongue as it extends towards the tongue's distal extremity. The observance system housing component also shows an opening 44 at the tray's distal extremity 40, which allows access to a communications port 45, such as a USB or micro-USB or mini-USB port, or the like, and/or a charging module located in the observance system housing component 12, to allow for a power supply also contained in said housing component 12 to receive electrical charge from an external power source. In a preferred embodiment, the opening 44 leads to a micro-USB port 45, which can be used at least for charging a power supply contained within the observance system housing, but additionally may also allow for communication between the add-on device and a separate device, such as a computer or docking station, or a programming unit, for example, to flash, wipe, reinstall or upgrade the observance system on the add-on device as required or appropriate.

Figure 4:
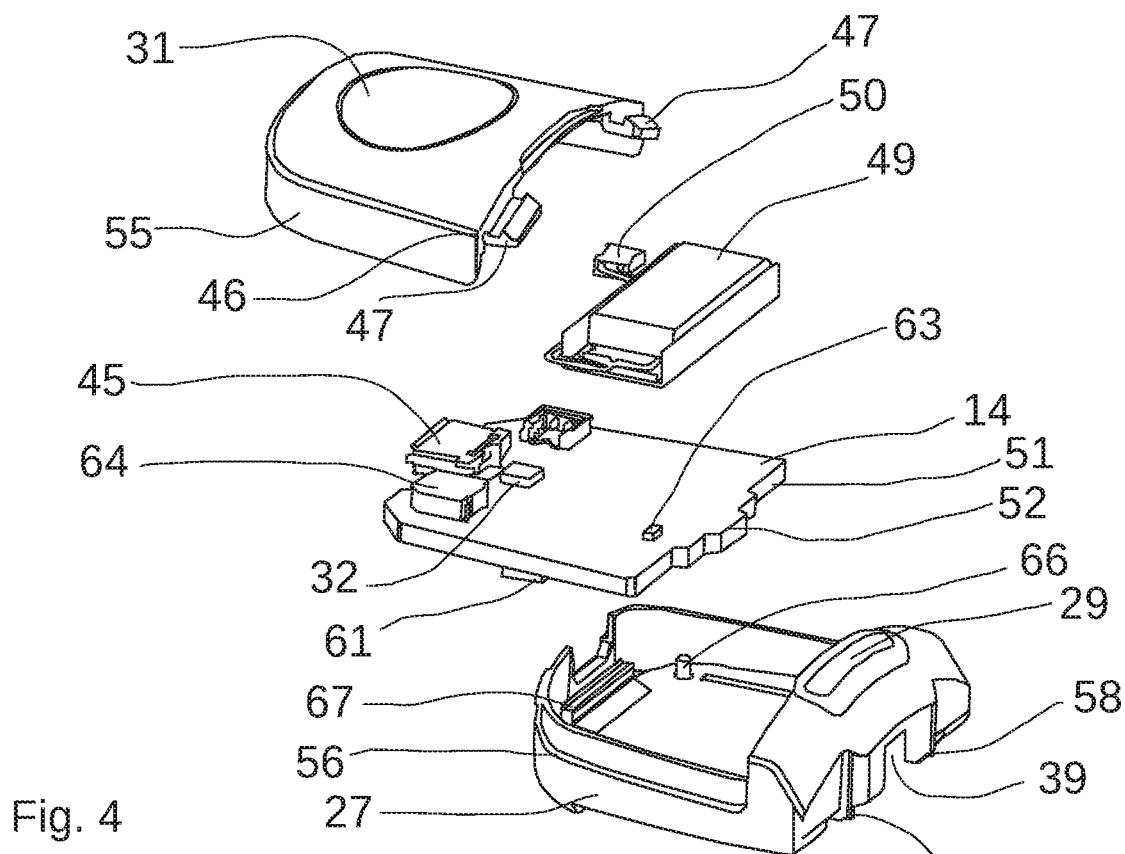
FIG. 4 is a schematic exploded view representation of the observance system housing component making up part of the add-on device of the present invention.

FIG. 4 shows an exploded view of the observance system housing component 12, in which the tray 27 and cover 28 are illustrated. Also shown is a printed circuit board 14, onto which the observance system comprising its various elements is mounted. At its proximal extremity 46, the cover or lid 28 is provided with two push-fit or snap-fit tongue projections 47, that are inserted into corresponding slots or openings provided within an inner proximal extremity of the body of the tray 27. The cover also contains a catch (not shown) at its distal extremity 48, which catch engages with a corresponding shoulder provided on the tray. The printed circuit board 14 is inserted into and held onto, the interior of the tray 27, and a power supply 49, for example, a removable and/or rechargeable battery, can be located on the circuit board 14 between the cover 28 and said circuit board 14. In FIGS. 1 and 4, the power supply 49 is a rechargeable lithium ion battery, which is connected to the circuit board 14 via an appropriately located connector 50, also provided on said circuit board 14. The printed circuit board 14 is positioned within the tray 27 at the board's proximal extremity 51 by a projection 52 provided on said circuit board which engages with a corresponding orifice 39 provided in the body of the tray 27 and rests on spigots 66 and a shoulder 67 located near the distal extremity and opening 44. The orifice 39 is sufficiently dimensioned to house both the projection 52 of the circuit board and allows for passage of air to flow over the circuit board and through said orifice 39 from and into the channel or groove 34 formed in the mouthpiece component 12. The air pressure sensor 54 is ideally located on the printed circuit board 14 in the area of airflow, as it will then lie directly in the air flow passage, and be able to detect corresponding air pressure change events, caused by inhalation, exhalation, holding of breath by the user, etc. FIG. 4 further shows that the cover 28 is provided with side walls 55, which are configured to mate with a corresponding shoulder 56 provided on the tray 27, thereby providing a complete enclosure of the observance system and forming the observance system housing 12.

Figure 5:
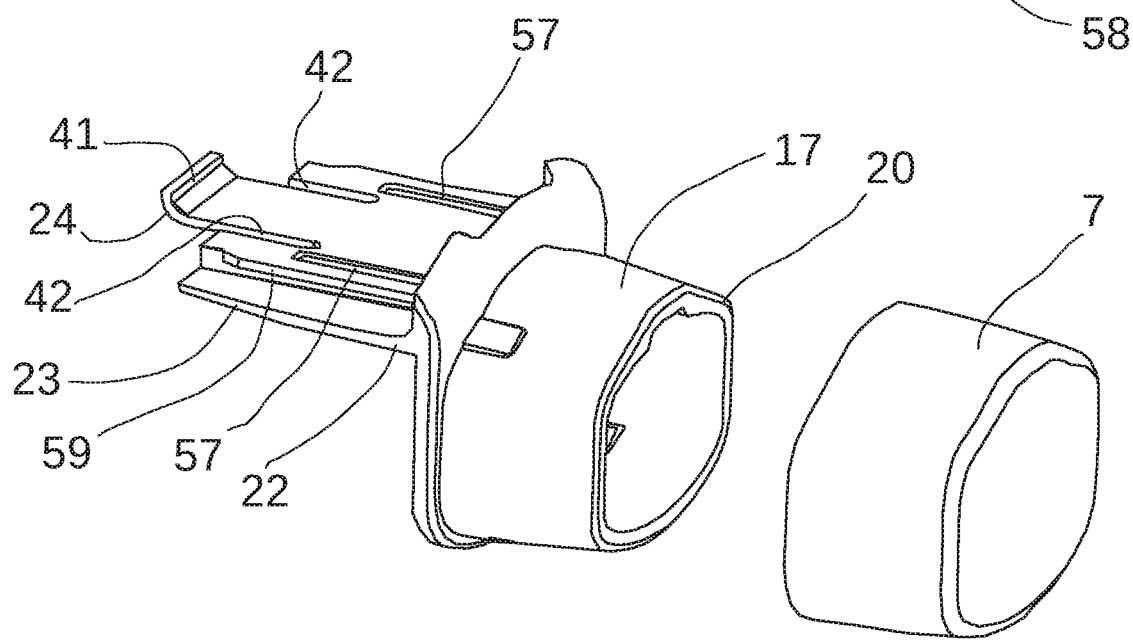
FIG. 5 is a schematic exploded view representation of the mouthpiece component making up part of the add-on device of the present invention.

FIG. 5 illustrates a schematic perspective view of the mouthpiece component 15 and a cap 7 for said mouthpiece component. The mouthpiece component 15 presents an annular mouthpiece with an outer peripheral surface 17 comprising grip means located thereon at the distal extremity 19 of the annular shaped mouthpiece component 15, enabling cap to frictionally engage with and be removed from the add-on device when required, e.g. for use of said device. Also shown in FIG. 5 is the tongue 22 and support plate 23, which extend in a substantially planar configuration towards a distal extremity 24. The distal extremity 24 of tongue 22 is preferably configured to form a curved lip, hook or edge, which wraps around a distal extremity 40 of tray 27, and is provided with engagement means 41 to removably engage with the distal extremity 40 of tray 27. Such removable engagement means 41 can be, for example, a snap-fit or click-fit projection provided at the distal extremity 24 of the tongue 22, and which is elastically insertable into a corresponding slot provided at the distal extremity 40 of the tray 27. The support plate 23, in the embodiment represented by FIG. 5, also shows two slots 42 provided in one of the surfaces of the plate 23. The slots 42 provide flexibility to the support plate and the tongue as it extends towards the tongue's distal extremity. The plate 23 also comprises two grooves or channels 57 also located in and extending along the plate of the tongue. These grooves 57 are sloped from the tongue surface inwards from their distal ends into the thickness of the plate and towards the distal extremity of the annular mouthpiece component. The grooves 57 are dimensioned to receive corresponding locating projections 58 situated on the tray 27 and which guide the tray along a substantially straight axis as the tray is slid onto and engages with the tongue plate 23 of the annular mouthpiece component. At the same time, the tongue plate 23 is also provided with substantially orthogonally projecting flanges 59 which extend from the plate 23 towards the outer edges of the plate. The flanges lie along substantially the same longitudinal axis as the grooves 57 and are designed to cooperate and engage with corresponding grooves provided on an outer surface of the tray 27 (shown in FIG. 6B described below).

Figure 6A:
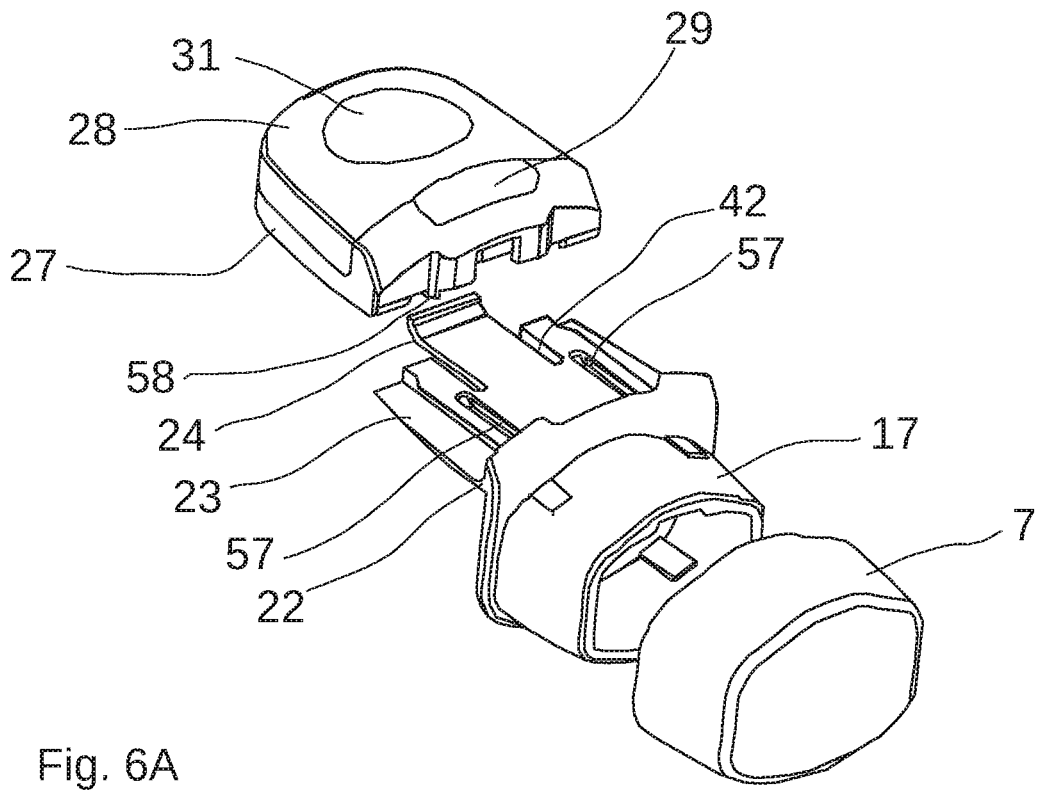
FIGS. 6A and 6B are schematic exploded view representations from reverse angles of the observance system housing component and the mouthpiece component of the add-on device according to the present invention, along with a cap for the mouthpiece component.
Figure 6B:
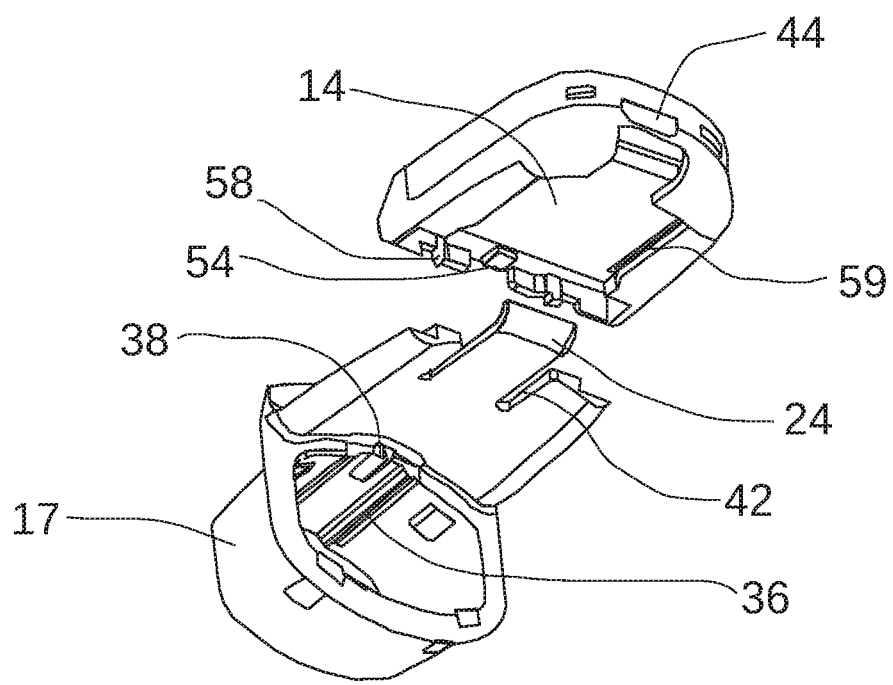

FIGS. 6A and 6B, in a manner similar to FIGS. 2 and 3, and show an exploded view of the add-on device of the invention from two perspective angles, FIG. 6A being a substantially reversed and flipped view of the add-on device of FIG. 6B. In FIG. 6A, one can understand how the lid and tray, assembled together, are located onto the plate 23 of the mouthpiece component 15. In FIG. 6B, on the other hand, one can understand how the tongue plate 23 and the distal extremity 24 of tongue 22 are preferably configured to form a curved lip, hook or edge, which wraps around a distal extremity 40 of tray 27, and is provided with engagement means 41 to removably engage with the distal extremity 40 of tray 27. Such removable engagement means 41 can be, for example, a snap-fit or click-fit projection provided at the distal extremity 24 of the tongue 22, and which is elastically insertable into a corresponding slot provided at the distal extremity 40 of the tray 27.

Figure 7:
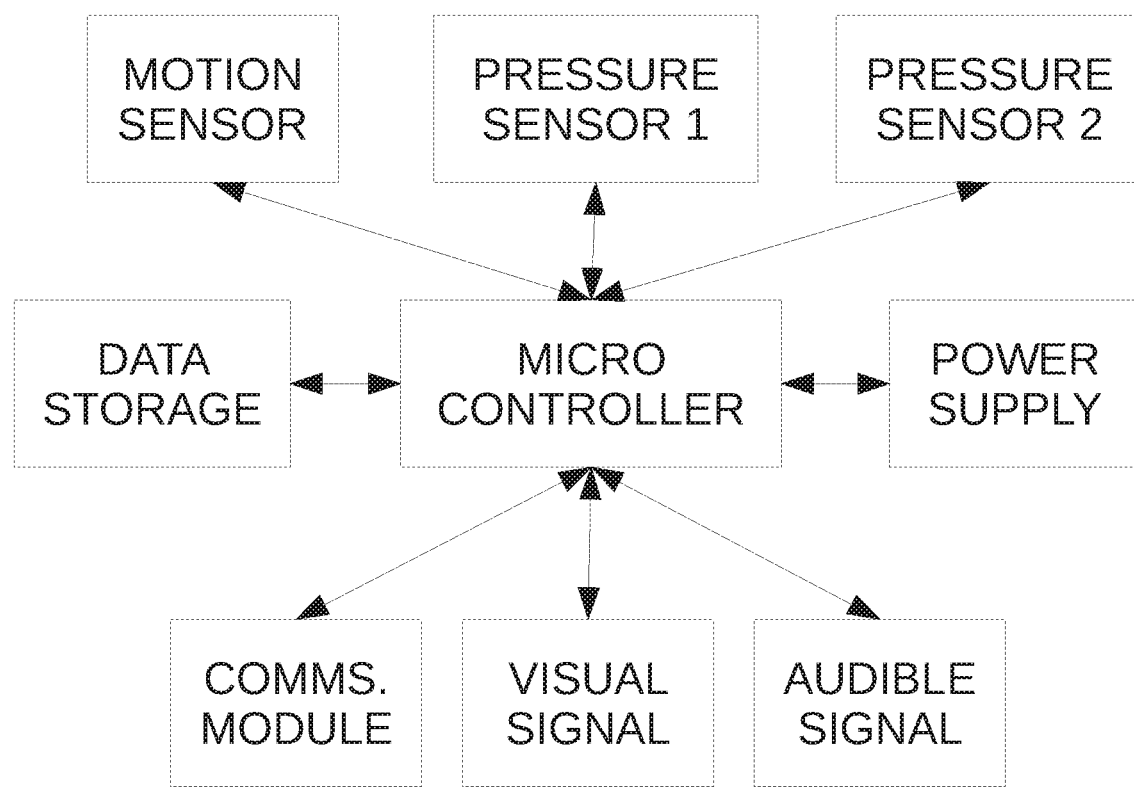
FIG. 7 is a schematic representation of the elements constituting the observance system according to the invention.

FIG. 7 is a schematic block representation of the observance system according to the present invention and adapted for use in the add-on device. The observance system as represented by FIG. 7 comprises a micro-controller 60, and various other elements connected thereto. The other elements constituting the observance system are a first pressure sensor (PS1), in this case an air pressure sensor 54, a second pressure sensor (PS2), in this case, a mechanical compression pressure sensor 32, a power supply 49, for example, as mentioned above, a rechargeable lithium ion battery, a motion sensor 61, a wireless communications module 62, identified as "Comms. Module" in FIG. 7, a visual signal means 63, an audible signal means 64, and a data storage module 65. The visual signal means 63 can comprise, as mentioned above, a LED display, consisting or one or multiple LEDs arranged appropriately. The audible signal means 64 can comprise, for example, a buzzer or other audible sound emitter. The wireless communications module 62 is preferably a Bluetooth low energy circuit, enabling short range communication with a remote device, such as a smartphone. Alternative wireless communication modules are also possible, for example, those communicating via the various wifi communications protocols, such as wifi-a, b, g, or n. The data storage module 65 can be any suitable module from the known types of data storage or to be developed, such as for example, ROM or RAM chips, solid state circuits, NAND circuits, chemical memory storage, and the like. The micro-controller 60 is responsible for controlling the various interactions between the components, registering and storing data or signals received therefrom or communicated thereto, and is therefore connected to the other components, but the micro-controller also effects calculations and determines various states allowing the observance system and add-on device to function as intended. The micro-controller 60 is also responsible for controlling the power supply 49 to the various elements of the observance system. Depending on a given state at any given time, the micro-controller 60 can send a wake up or sleep call to the components, and provide power the other components, or shutdown power access to said components, in order to manage power consumption in the most effective manner.

In the following description of how the observance system functions and corresponding figures, the following acronyms, relating to constants and variables of the system are defined as follows:

Constants:

TABLE 1

| Constant | Constant Name | Definition |
|---|---|---|
| ILV | Interrupt Level | $1\ G \leq IL \leq 3\ G$ |
| NSI | Number of Successive Interrupts | $2 \leq NSI \leq 5$ |
| TMB | Maximum Pressure Buffer Window Time | $15\ s \leq TMB \leq 60\ s$ |
| TMA | Buffer Start Time Margin | $0.5\ s \leq TMA \leq 5\ s$ |
| TSR | Time at which recording is stopped when no respiratory activity has | $1\ s \leq TSR \leq 15\ s$ |

TABLE 1-continued

| Constant | Constant Name | Definition |
|---|---|---|
| | occurred since previous recorded respiratory activity and before TMB has been reached | |
| TMR | Maximum Recording Time | =TMB − TMA |
| TDI | Device Inactive Time | 5 s ≤ TDI ≤ 60 s |

Variables:

TABLE 2

| Acronym | Variable |
|---|---|
| I | Instant time |
| IDR | Time recorded at drug release |
| IRA | Time recorded at beginning of respiratory activity |
| ISA | Time recorded at end of respiratory activity |
| ILA | Time recorded of last respiratory activity |

Figure 8:
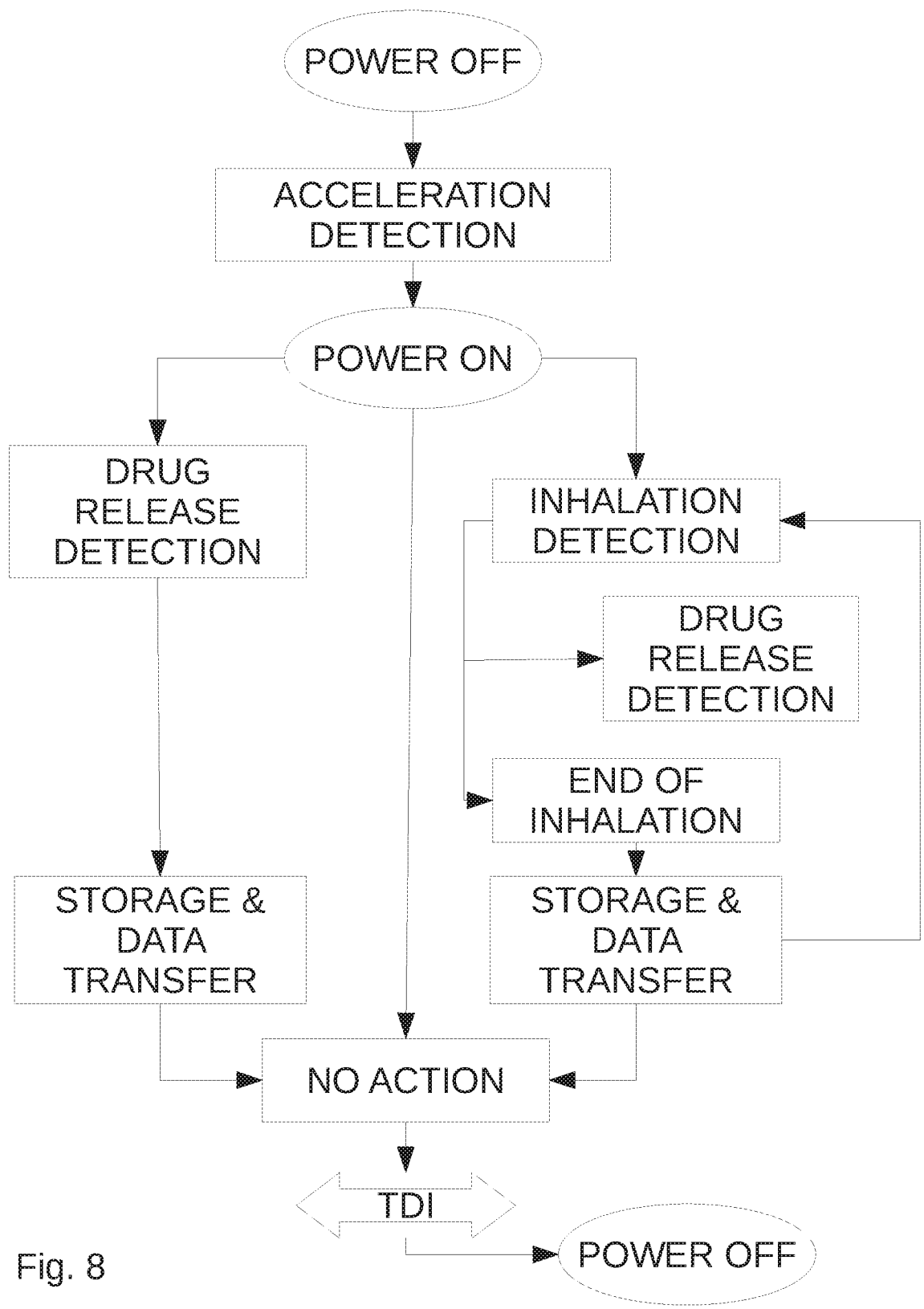
FIG. 8 is a schematic flow chart of one way of functioning of the observance system according to the invention.

Turning now to FIG. 8, a general schema of one way in which the observance system can be configured to function is displayed. As can be seen from FIG. 8, the observance system, for example, contained within an observance system housing 12 as described above, is generally in a sleep, or slumber or hibernation mode. This mode allows for the observance system to register certain predefined events, as will be explained hereafter, without wasting too much of the power supply, especially if this is a rechargeable battery, for example. In other words, the system is powered on, but using only the minimum of power. Testing by the applicant has shown that favorable results have been obtained when only the motion sensor 61 is supplied with power in sleep mode, and the other elements, apart from the micro-controller 60, and the power supply 49 itself, are activated. In this way, when the device is shaken by a user, the motion sensor 61 can detect a movement of acceleration and this is registered with the micro-controller, for example, stored in data storage or exploited directly. The micro-controller 60 is configured to be able to determine the difference between an accidental movement of acceleration registered by the motion sensor 61, for example, such as when the add-on device gets accidentally knocked or dropped, and a voluntary movement of acceleration, for example, due to the user shaking the device repeatedly. On receiving such a signal of, the micro-controller 60 therefore allows power to be supplied to the other components, such that the remainder of the device effectively awakens. The micro-controller 60 then enters a wait state for a predetermined length of time, waiting for a signal from pressure sensor (PS2) 32, i.e. a mechanical compression, such as the action of a user pressing the housing 12 with its thumb, or compressing the housing between thumb and finger when the user presses down on the cartridge 3 of the MDI. If such a pressure signal is detected and registered by the pressure sensor (PS2) 32, it is stored in the data storage, or otherwise evaluated by the micro-controller. At the same time as, or subsequently to, detecting a suitable from pressure sensor (PS2) 32, the micro-controller 60 can also wait for detection of a signal from air pressure sensor (PS1) 54, indicating that an air pressure change event has occurred. Such air pressure change events generally occur when the user inhales, or exhales, or stops breathing, through the device. In FIG. 8, the event registered is an inhalation event, which cause a pressure drop across the pressure sensor (PS1) 54 as air is withdrawn by the user through the observance system housing 12 and the mouthpiece component 15, as drug, which has been delivered by the user pressing on the cartridge, is inhaled. When the user stops inhaling, there is generally another pressure change event, and this too can be stored by the micro-controller, or evaluated as appropriate. The period followed by the end of inhalation is generally followed by an increase in air pressure across the pressure sensor (PS1) 54, as the system re-equilibrates to ambient air pressure. All of these pressure change events can be registered by the pressure sensor (PS1) 54 and signalled to the micro-controller for storage and/or evaluation. Once sufficient data has been stored, it is transmitted via the communications module, e.g. via Bluetooth, to a software application running on a remote device, such as a smartphone, or a remote server, or distributed network. From there the data can be either further evaluated, and/or displayed in a meaningful way to either the user, as a way of assisting the user in observing its treatment regime, or to a healthcare professional, enabling the latter to make or recommend any adjustments to the treatment regime, or simply provide the user with guidance for improving said treatment. After data transmission has completed, or alternatively, if no events are registered that correspond to those required to be considered as meeting the criteria of a drug release and subsequent inhalation of drug within a given timeframe, identified as the device inactive time (TDI) on FIG. 8, then the micro-controller sends out a signal the system to put the device back into sleep mode. An advantageous device inactivity time (TDI) in accordance with the present invention has been determined to be in the range of between about 5 seconds to about 60 s.

Figure 9:
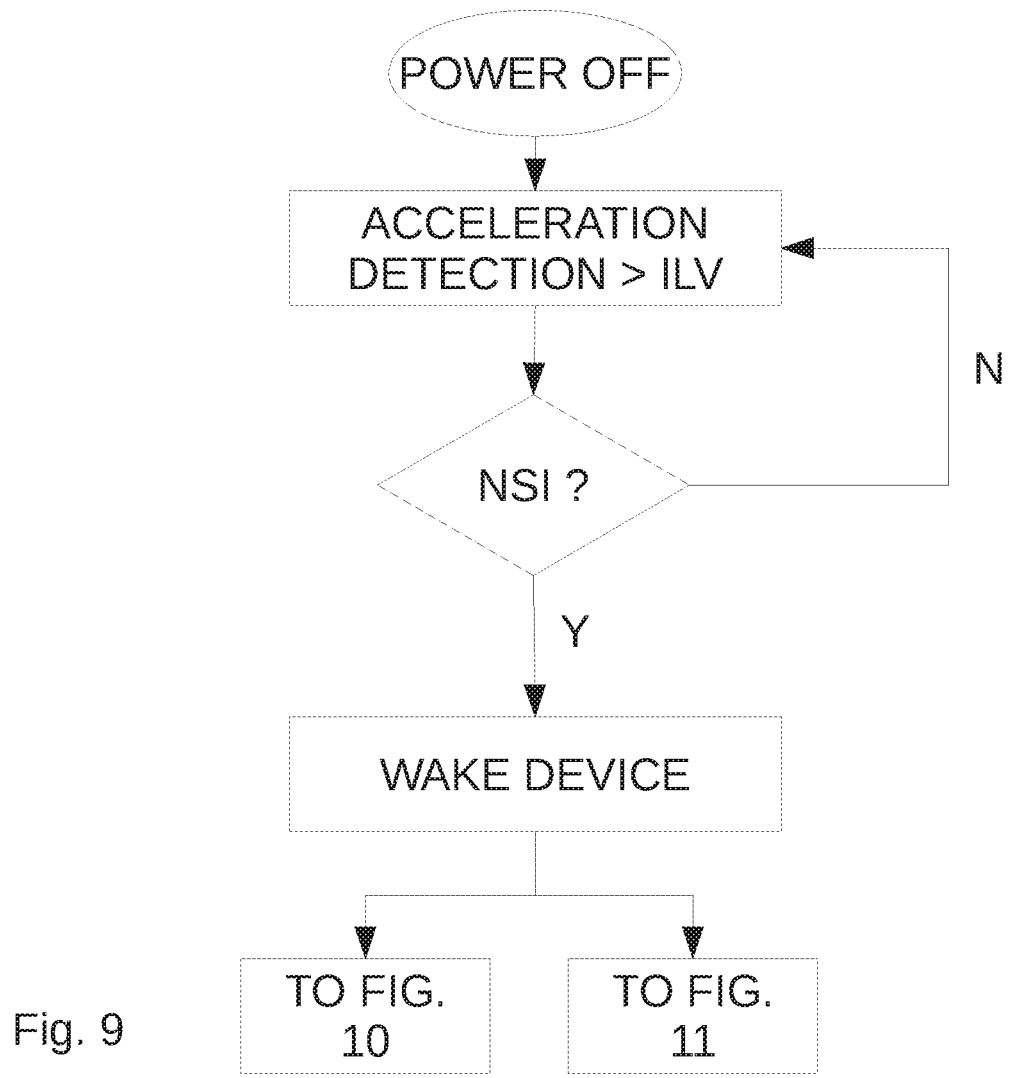
FIG. 9 is a schematic flow chart of another way of functioning of the observance system according to the invention.

As will be understood from the preceding description, the system is therefore configured to record, among others:
drug release events;
respiratory activity events;
maximum buffer elapsed time (TMB);
buffer window start time: which is calculated from TMA and therefore occurs before any first respiratory activity; and
buffer window stop time (TSR). Looking now in detail at the functioning of the observance system, FIG. 9 shows a schema of how the system functions when a movement of acceleration is registered or detected. In order to avoid incorrectly registering or detecting a sudden involuntary movement which might trigger the awakening of the system, the micro-controller 60 is configured to only react when a certain number of movements of acceleration are registered or detected by the motion sensor 61, and then only when said movements of acceleration exceed a predetermined value. As indicated schematically in FIG. 9, when such movements of acceleration are detected or registered by the motion sensor 61, an interrupt is generated. In order for the system to enter "awake" mode, the micro-controller is configured to take notice of a successive sequence of interrupts, generally between two and five successive interrupts, and preferably three successive interrupts, whereby each interrupt corresponds to a movement of acceleration that is between approximately 1G to 3G, and preferably is from 2G to 2.5G. These values and number of interrupts corresponds to the values registered when the user primes the MDI by shaking it from side to side or up and down in quick succession, i.e. preparing or priming the MDI for delivery or release of drug. In this way, the remainder of the components are only awakened for further action if those conditions are met, thereby avoiding that the system is placed in the "awake" state when it is not required. If none of the conditions are met for a period of time corresponding to the device inactivity time (TDI), then the system returns to the sleeping state.

Figure 10:
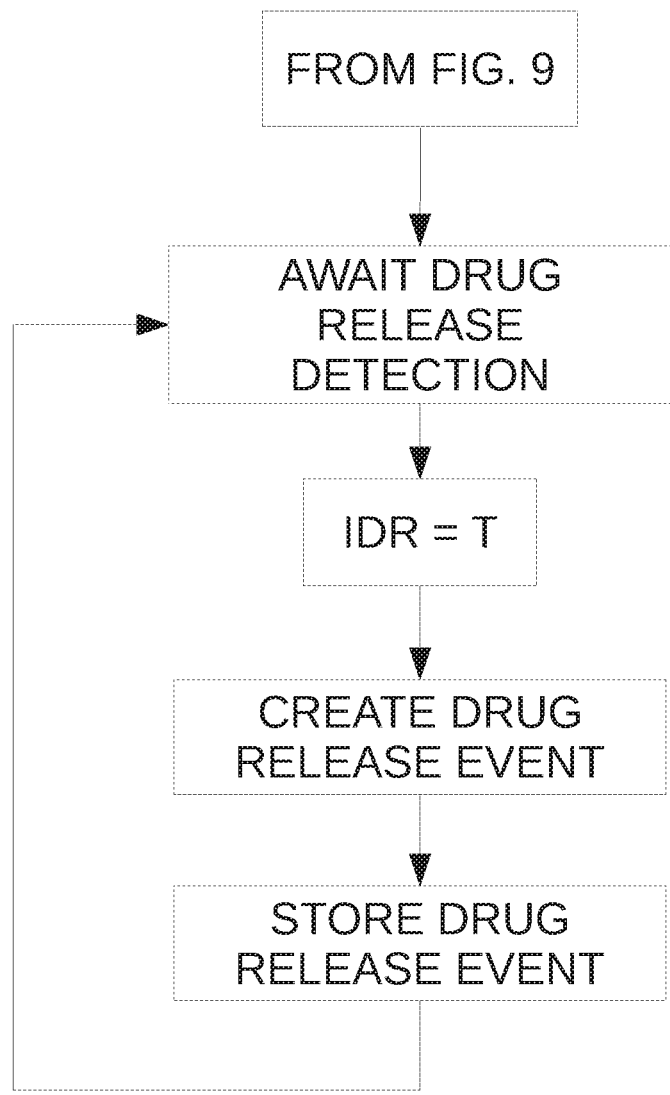
FIG. 10 is a schematic flow chart following on from that of FIG. 9.

FIG. 10 illustrates the schematic functioning of the events linked to drug release. In the awake state, i.e. coming from FIG. 9, the system waits for a pressure change event to be registered or detected at said pressure sensors (PS2) 32, and a corresponding signal sent to the micro-controller 60. Only the pressure signal corresponding to a predetermined mechanical pressure exerted on the sensor or the observance system housing, and corresponding to pressing of the cartridge by the user to release drug, is handled by the micro-controller. The time at which such an event occurs is registered within the system, and called the drug release time (IDR). Registration of this time also leads to creation of an event called the release event, indicating to the system that the drug has been released for delivery, in other words, that the user has pressed the cartridge down in the MDI and released the drug formulation into the mouthpiece outlet of the MDI. The release event is stored for further processing and/or data transmission as required and the loop returns to await the next pressure signal event, for example, if the user presses down on the cartridge once again, in so doing, compresses the pressure sensor PS2 32. Although not shown in FIG. 10, the loop is also on the same time limit or device inactivity time (TDI), after which, if no release event is registered, the device is returned to sleep mode.

Figure 11:
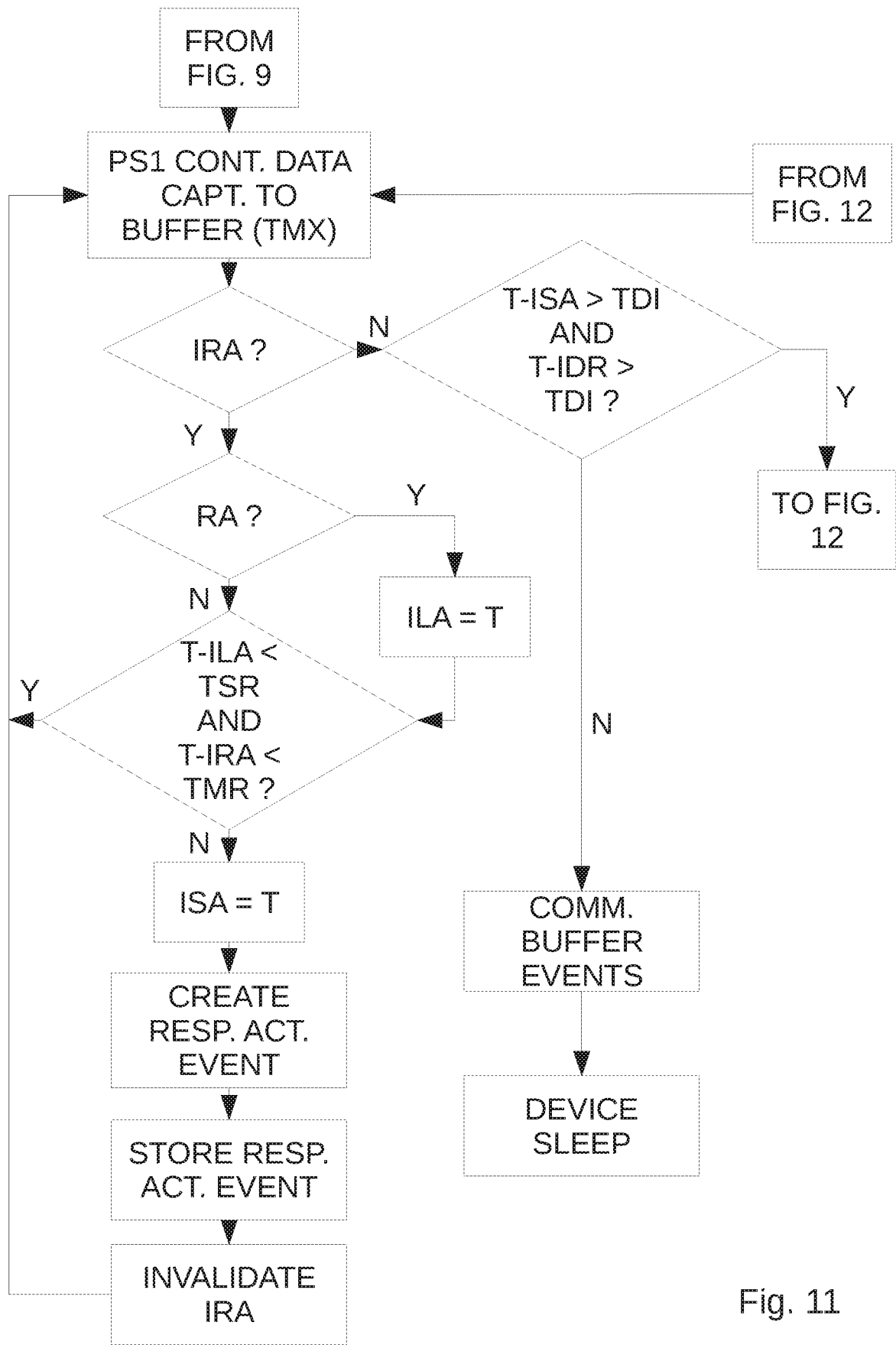
FIG. 11 is a schematic flow chart following on from that of FIG. 10.

Turning now to FIG. 11, a schematic representation of the inhalation event loop functioning is shown. In this schema, with the system in the "awake" state as indicated, coming from FIG. 9, air pressure sensor data received from pressure sensor (PS1) 54 is registered continuously in a buffer as indicated in the box titled "PS1 CONT DATA CAPT. TO BUFFER (TMB)". The buffer only stores data received for a continuous rolling window of predetermined elapsed time (TMB).

The applicants have determined that a maximum rolling buffer time (TMB) window of greater or equal to 15 seconds and less than or equal to 60 seconds is an advantageous period of time to be able to gather enough data for further accurate processing. In a first step, the micro-controller determines whether a start time for respiratory activity (IRA) has been registered with the system. If the result of that determination is positive, then a determination is made as to whether a respiratory event has been detected. If a respiratory event has been detected, then a time at which a last respiratory activity (ILA) was recorded is defined as being equal to the current or instant time registered by the system, and then moves on to the following determination described hereafter. If no respiratory event has been detected, then the system moves straight into the following determination of whether two conditions are both met, namely:

current time T minus the last respiratory activity time (ILA) is less than the time (TSR) at which recording was stopped when no respiratory activity had occurred since previous recorded respiratory activity and before TMB was been reached;
and
current time T minus the respiratory start time (IRA) is less than the maximum recording time (TMR).

In the above determination, the applicant has determined that the TSR is advantageously between greater than or equal to is and less than or equal to 15 s.

If the outcome of this determination is also positive, then the loop returns to the continuous air pressure sensor (PS1) 54 data collection state to await more data. If the outcome of this determination is negative, then the value of the respiratory activity end time (ISA), i.e. when an inhalation ends, is defined as being equal to the actual current time recorded by the system. In this case, an inhalation event is created, and the data extracted from the buffer between the respiratory activity start time (IRA) and the respiratory activity end time (ISA) are stored in the system for further processing and or data communication. Finally, the respiratory activity start time (IRA) value is invalidated and the loop returns to the continuous air pressure sensor (PS1) 54 data collection state to await more data. If, in the first step, the determination of a respiratory activity start time (IRA) is negative, then a further determination is made, wherein a test for both of the following conditions occurs:

current recorded time T minus the respiratory end time (ISA) is greater than the device inactivity time (TDI);
and
current recorded time T minus the drug release time (IDR) is greater than the device inactivity time (TDI).

Figure 12:
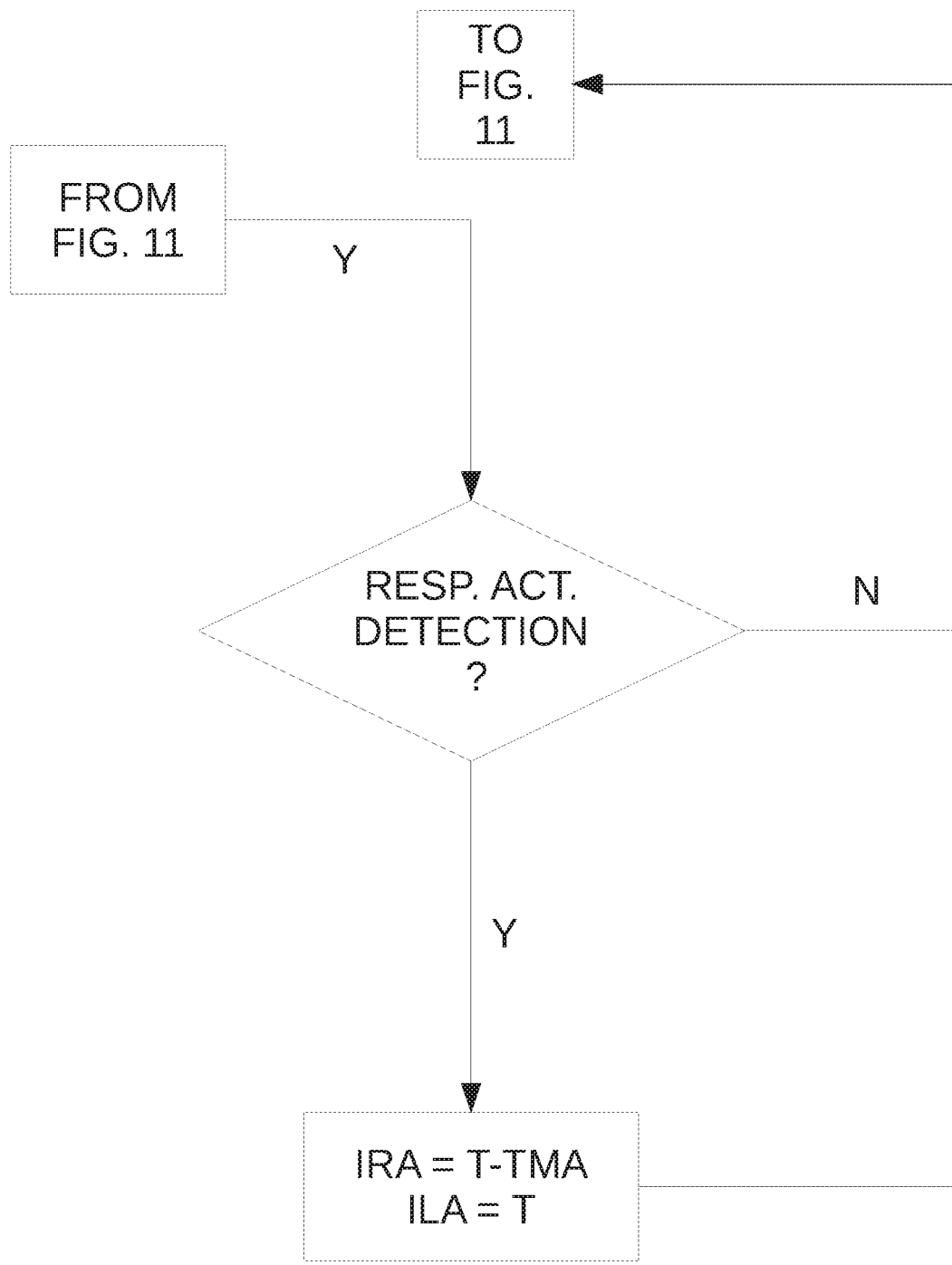
FIG. 12 is a schematic flow chart following on from and linked back to that of FIG. 11.

If the outcome of this determination is positive, i.e both conditions are met, then the system enters a respiratory activity detection loop as illustrated in FIG. 12. If the outcome is negative, however, then the system transmits any data recovered from the buffer via the communications module, to the remote device, and then the system returns to the sleeping state.

FIG. 12 is a continuation of FIG. 11, and is a schematic illustration of the inhalation activity detection loop used by the system to determine when an inhalation has commenced. In this loop a determination is first made as to whether an inhalation event has been detected. Where the outcome to this determination is positive, then the respiratory activity start time (IRA) value is set to the current time T recorded by the system minus the buffer start time margin (TMA), and additionally, the previous respiratory activity time value (ILA) is set to current time T recorded by the system, and then the loop returns to the continuous data capture of the air pressure sensor (PS1) 54 as illustrated by the arrow pointing back to FIG. 11. If no respiratory activity has been detected, then the system also returns to continuous data capture of the air pressure sensor (PS1) 54, as illustrated by the arrow pointing back to FIG. 11.

The invention claimed is:

1. Method for improving observance of delivery of a drug delivered via a metered dose inhaler, said method comprising:
fitting an add-on device to an exterior surface of a mouthpiece outlet of a metered dose inhaler, said add-on device comprising:
a housing;
an observance system including: a micro-controller and at least one or more elements selected from a data storage means, a visual signal producing means, an audible signal producing means, a power supply, a wireless communications module, a first pressure sensor, a second pressure sensor, a motion sensor, and a communications port, each of said at least one or more elements being connected to said micro-controller; and
a mouthpiece component having a wall defining a channel and an inhaler opening, said wall is configured to fit, surround and removably engage with an exterior surface of the mouthpiece outlet provided on the metered dose inhaler such that at least a portion of said wall is insertable into a mouth of a user and such that medication flow from the mouthpiece outlet of the metered dose inhaler is inhaled through the inhaler opening;

wherein said housing is configured to fit and removably engage with said mouthpiece component;

wherein said mouthpiece component is specifically adapted such that an interior surface of the wall of the mouthpiece component elastically engages with and rests on the exterior surface of the mouthpiece outlet of the metered dose inhaler without obstructing delivery of a dose of drug through said mouthpiece outlet; and wherein the add-on device does not create any supplemental chamber through which the drug would have to pass, in addition to a chamber already provided by the metered dose inhaler;

registering at least one or more vibration events of a predetermined magnitude received from the motion sensor and turn on the add-on device when a vibration event of a particular magnitude is registered by the micro-controller;

detecting a pressure change event at the second pressure sensor corresponding to pressing a drug cartridge of the metered dose inhaler to release drug through the mouthpiece of the metered dose inhaler;

detecting an onset of inhalation via a pressure change event registered at the first sensor;

detecting an end of inhalation via a pressure change event at said first pressure sensor;

communicating data pertaining to at least one sensor event to a software application executing on a remote device, a remote server or a distributed network system;

presenting said data to a user of the device or a healthcare professional in a manner enabling said user or healthcare professional to see whether the drug has been inhaled correctly.

2. Method according to claim 1, further comprising activating a visual signal or an audible signal indicating correct level of remaining power supply.

3. Method according to any one of claim 1, further comprising activating a visual signal or an audible signal indicating correct priming of drug to be delivered.

4. Method according to any one of claim 1, further comprising activating a visual signal and/or an audible signal indicating correct inhalation of drug delivered through the mouthpiece.

5. Method according to any one of claim 1, further comprising activating a visual signal and/or an audible signal indicating the location and/or position of the add-on device.

6. Method according to any one of claim 1, wherein the observance system is further configured to store within the device a number of drug doses delivered by the metered dose inhaler.

7. Method according to any one of claim 1, wherein the observance system is further configured to store within the device a number of drug doses remaining in the metered dose inhaler.

8. Method according to any one of claim 1, wherein the observance system is further configured to store within the device a power supply level.

9. Method according to any one of claim 1, wherein the observance system is further configured to store within the system a wake up time of the observance system.

10. Method according to any one of claim 1, wherein the observance system is further configured to store within the device a priming time of said metered dose inhaler.

11. Method according to any one of claim 1, wherein the observance system is further configured to store within the device a drug release time from said metered dose inhaler.

12. Method according to any one of claim 1, wherein the observance system is further configured to store within the device a time of onset of inhalation of released drug.

13. Method according to any one of claim 1, wherein the observance system is further configured to store within the device a time of end of inhalation of released drug.

14. Method according to any one of claim 1, wherein the observance system is further configured to communicate any of the data, signals or time events to the remote device, the remote server or the distributed network system.

15. Method according to any one of claim 1, wherein said remote device is a mobile telephone or smartphone.

16. Method according to claim 1, wherein the at least one or more vibration events of a predetermined magnitude received by the micro-controller from the motion sensor has a movement of acceleration of between 1G to 3G.

17. Method according to claim 1, wherein the micro-controller is configured to register two to five successive vibration events received from the motion sensor, whereby each vibration event has a movement of acceleration of between 1G to 3G.

* * * * *